US005652222A

United States Patent [19]
Calabretta et al.

[11] Patent Number: 5,652,222
[45] Date of Patent: Jul. 29, 1997

[54] SELECTIVE INHIBITION OF LEUKEMIC CELL PROLIFERATION BY BCR-ABL ANTISENSE OLIGONUCLEOTIDES

[75] Inventors: Bruno Calabretta; Alan M. Gewirtz, both of Philadelphia, Pa.

[73] Assignee: Temple University-of The Commonwealth System of Higher Education, Philadelphia, Pa.

[21] Appl. No.: 152,621

[22] Filed: Nov. 15, 1993

Related U.S. Application Data

[63] Continuation of Ser. No. 869,911, Apr. 14, 1992, abandoned, which is a continuation-in-part of Ser. No. 718,302, Jun. 18, 1991, abandoned.

[51] Int. Cl.$^6$ .......................... A61K 48/00; C07H 21/04; C12N 15/00; C12N 5/00
[52] U.S. Cl. .................. 514/44; 536/24.5; 435/172.3; 435/375; 935/62
[58] Field of Search ...................... 514/44; 536/24.5; 424/93.21; 435/172.3, 240.1, 62

[56] References Cited

U.S. PATENT DOCUMENTS

| | | |
|---|---|---|
| 4,681,840 | 7/1987 | Stephenson et al. . |
| 4,857,466 | 8/1989 | Saunders et al. . |
| 4,874,853 | 10/1989 | Rossi . |
| 5,087,617 | 2/1992 | Smith . |
| 5,098,890 | 3/1992 | Gewirtz et al. . |

FOREIGN PATENT DOCUMENTS

| | | |
|---|---|---|
| WO89/09285 | 10/1989 | WIPO . |
| WO91/04753 | 4/1991 | WIPO . |

OTHER PUBLICATIONS

Kawasaki et al (1988) Proced. Natl. Acad. Sci. 85, 5698–5702.
Harrison's Principles of Internal Medicine, vol. 2, 1994, pp. 1757–1764.
Tseng et al (1994) Cancer Gene Therapy 1, 65–71.
deFabritis et al (1995) Leukemia 9, 662–664.
Daley et al., Science 247, 824–830 (1990).
Heisterkamp et al., Nature 344, 251–253 (1990).
Caracciolo et al., Science 245, 1107–1110 (1989).
Kawasaki et al., Proc. Natl. Acad. Sci. USA 85, 5698–5702 (1988).
Yuan et al., Clin Res. 39, (2) (abs. 211A) (Apr. 19, 1991).
Yuan et al., J. Cellular Biochem., Supp. 15D, 37 (Feb. 2, 1991).
Han et al. Proc. Natl. Acad. Sci. 88, 4313–4317 (1991).
Anfossi et al., Proc. Natl. Acad. Sci. 86, 3379–3383 (1989).
Kitajima et al., Science 258, 1792–1795 (1992).
Levy, "Interferon and Interferon Inducers", Marcel Dekker, Inc., New York and Basel, 167–185 (1980).
Madaio et al, The J. of Immunology, 137, 2535–2540 No. 8 (1986).
Majello et al., Proc. Natl. Acad. Sci. USA 83, 9636–9640 (1986).
Gewirtz et al., Science 242, Reports: 1303–1306 (1988).
Gewirtz et al., Science 245, Reports: 180–183 (1989).

*Primary Examiner*—Jasemine C. Chambers
*Assistant Examiner*—Deborah Crouch
*Attorney, Agent, or Firm*—Seidel, Gonda, Lavorgna & Monaco, PC

[57] ABSTRACT

Leukemias characterized by the presence of the Philadelphia chromosome and the expression of the hybrid bcr-abl gene are treated with antisense oligonucleotides complementary to a target sequence of the bcr-abl mRNA transcript including the breakpoint junction. Individual chronic myelogoneous leukemia patients or Philadelphia chromosome-positive acute lymphocytic leukemia patients are treated by first sequencing the individual's bcr-abl breakpoint junction, and then administering antisense oligonucleotides complementary thereto. The oligonucleotides are designed to hybridize specifically to the bcr-abl breakpoint junction without substantial cross hybridization to untranslocated c-abl sequences. Treatment may comprise in vivo administration of antisense oligonucleotides, or ex vivo treatment such as bone marrow purging.

69 Claims, 10 Drawing Sheets

FIG. 1

| | | | | |
|---|---|---|---|---|
| CACAGCATTC | CGCTGACCAT | CA\|ATAAGGAA | G↓AAGCCCTTC\| | 40 |
| AGCGGCCAGT | AGCATCTGAC | TTTGAGCCTC | AGGGTCTGAG | 80 |
| TGAAGCCGCT | CGTTGGAACT | CCAAGGAAAA | CCTTCTCGCT | 120 |
| GGACCCAGTG | AAAATGACCC | CAACCTTTTC | GTTGCACTGT | 160 |
| ATGATTTGT | GGCCAGTGGA | GATAACACTC | TAAGCATAAC | 200 |
| TAAAGGTGAA | AAGCTCCGGG | TCTTAGGCTA | TAATCACAAT | 240 |
| GGGGAATGGT | GTGAAGC | | | |

FIG. 3

| | | | | |
|---|---|---|---|---|
| GTCATCGTCC | ACTCAGCCAC | TGGATTTAAG | C\|AGAGTTCAA↓ | 40 |
| ↓\|AAGCCCTTC\|A | GCGGCCAGTA | GCATCTGACT | TTGAGCCTCA | 80 |
| GGGTCTGAGT | GAAGCCGCTC | GTTGGAACTC | CAAGGAAAAC | 120 |
| CTTCTCGCTG | ACCCAGTGA | AAATGACCCC | AACCTTTTCG | 160 |
| TTGCACTGTA | TGATTTTGTG | CCAGTGGAG | ATAACACTCT | 200 |
| AAGCATAACT | AAAGGTGAAA | AGCTCCGGGT | CTTAGGCTAT | 240 |
| AATCACAATG | GGAATGGTG | TGAAGC | | |

FIG. 5

| | | | | |
|---|---|---|---|---|
| GATGGCGAGG | GCGCCTTCCA | TG\|GAGACGCA | G↓AAGCCCTTC\| | 40 |
| AGCGGCCAGT | AGCATCTGAC | TTTGAGCCTC | AGGGTCTGAG | 80 |

SENSE

ANTISENSE

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 257 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:1:

```
CACAGCATTC  CGCTGACCAT  CAATAAGGAA  GAAGCCCTTC    40
AGCGGCCAGT  AGCATCTGAC  TTTGAGCCTC  AGGGTCTGAG    80
TGAAGCCGCT  CGTTGGAACT  CCAAGGAAAA  CCTTCTCGCT   120
GGACCCAGTG  AAAATGACCC  CAACCTTTTC  GTTGCACTGT   160
ATGATTTGT   GGCCAGTGGA  GATAACACTC  TAAGCATAAC   200
TAAAGGTGAA  AAGCTCCGGG  TCTTAGGCTA  TAATCACAAT   240
GGGGAATGGT  GTGAAGC  257
```

( 2 ) INFORMATION FOR SEQ ID NO:2:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:2:

```
GAACGGCATC  TACGTTAT  18
```

( 2 ) INFORMATION FOR SEQ ID NO:3:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:3:

```
GAAGGGCTTC  TTCCTTAT  18
```

( 2 ) INFORMATION FOR SEQ ID NO:4:

( i ) SEQUENCE CHARACTERISTICS:
    ( A ) LENGTH: 266 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:4:

```
GTCATCGTCC  ACTCAGCCAC  TGGATTTAAG  CAGAGTTCAA    40

AAGCCCTTCA  GCGGCCAGTA  GCATCTGACT  TTGAGCCTCA    80

GGGTCTGAGT  GAAGCCGCTC  GTTGGAACTC  CAAGGAAAAC   120

CTTCTCGCTG  GACCCAGTGA  AAATGACCCC  AACCTTTTCG   160

TTGCACTGTA  TGATTTTGTG  GCCAGTGGAG  ATAACACTCT   200

AAGCATAACT  AAAGGTGAAA  AGCTCCGGGT  CTTAGGCTAT   240

AATCACAATG  GGGAATGGTG  TGAAGC      266
```

( 2 ) INFORMATION FOR SEQ ID NO:5:

( i ) SEQUENCE CHARACTERISTICS:
    ( A ) LENGTH: 18 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:5:

```
GAAGTGCTGT  TGAACTCT    18
```

( 2 ) INFORMATION FOR SEQ ID NO:6:

( i ) SEQUENCE CHARACTERISTICS:
    ( A ) LENGTH: 18 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:6:

```
GAAGGGCTTT  TGAACTCT    18
```

( 2 ) INFORMATION FOR SEQ ID NO:7:

( i ) SEQUENCE CHARACTERISTICS:
    ( A ) LENGTH: 80 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:7:

```
GATGGCGAGG  GCGCCTTCCA  TGGAGACGCA  GAAGCCCTTC    40

AGCGGCCAGT  AGCATCTGAC  TTTGAGCCTC  AGGGTCTGAG    80
```

( 2 ) INFORMATION FOR SEQ ID NO:8:

( i ) SEQUENCE CHARACTERISTICS:
    ( A ) LENGTH: 18 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:8:

```
GCAGGGCTTC  TACGTCTC    18
```

( 2 ) INFORMATION FOR SEQ ID NO:9:

( i ) SEQUENCE CHARACTERISTICS:
            ( A ) LENGTH: 18 Nucleotides
            ( B ) TYPE: nucleic acid
            ( C ) STRANDEDNESS: double stranded
            ( D ) TOPOLOGY: linear ( x i ) SEQUENCE DESCRIPTION: SEQ ID NO:9:

GAAGGGCTTC TGCGTCTC            18

( 2 ) INFORMATION FOR SEQ ID NO:10:

( i ) SEQUENCE CHARACTERISTICS:
            ( A ) LENGTH: 22 Nucleotides
            ( B ) TYPE: nucleic acid
            ( C ) STRANDEDNESS: single stranded
            ( D ) TOPOLOGY: linear ( x i ) SEQUENCE DESCRIPTION: SEQ ID NO:10:

GCTTCACACC ATTCCCCATT GT            22

( 2 ) INFORMATION FOR SEQ ID NO:11:

( i ) SEQUENCE CHARACTERISTICS:
            ( A ) LENGTH: 22 Nucleotides
            ( B ) TYPE: nucleic acid
            ( C ) STRANDEDNESS: double stranded
            ( D ) TOPOLOGY: linear ( x i ) SEQUENCE DESCRIPTION: SEQ ID NO:11:

CACAGCATTC CGCTGACCAT CA            22

( 2 ) INFORMATION FOR SEQ ID NO:12:

( i ) SEQUENCE CHARACTERISTICS:
            ( A ) LENGTH: 22 Nucleotides
            ( B ) TYPE: nucleic acid
            ( C ) STRANDEDNESS: single stranded
            ( D ) TOPOLOGY: Not Relevant ( x i ) SEQUENCE DESCRIPTION: SEQ ID NO:12:

GTCATCGTCC ACTCAGCCAC TG            22

( 2 ) INFORMATION FOR SEQ ID NO:13:

( i ) SEQUENCE CHARACTERISTICS:
            ( A ) LENGTH: 22 Nucleotides
            ( B ) TYPE: nucleic acid
            ( C ) STRANDEDNESS: single stranded
            ( D ) TOPOLOGY: linear ( x i ) SEQUENCE DESCRIPTION: SEQ ID NO:13:

CAACAGTCCT TCGACAGCAG CA            22

( 2 ) INFORMATION FOR SEQ ID NO:14:

( i ) SEQUENCE CHARACTERISTICS:
            ( A ) LENGTH: 18 Nucleotides
            ( B ) TYPE: nucleic acid
            ( C ) STRANDEDNESS: single stranded
            ( D ) TOPOLOGY: linear ( x i ) SEQUENCE DESCRIPTION: SEQ ID NO:14:

GAGACGCAGA AGCCCTTC            18

( 2 ) INFORMATION FOR SEQ ID NO:15:

( i ) SEQUENCE CHARACTERISTICS:
            ( A ) LENGTH: 14 Nucleotides (B) TYPE: nucleic acid
(C) STRANDEDNESS: single stranded
(D) TOPOLOGY: linear (xi) SEQUENCE DESCRIPTION: SEQ ID NO:15:

AGGGCTTCTT CCTT 14

(2) INFORMATION FOR SEQ ID NO:16:

(i) SEQUENCE CHARACTERISTICS:
(A) LENGTH: 16 Nucleotides
(B) TYPE: nucleic acid
(C) STRANDEDNESS: single stranded
(D) TOPOLOGY: linear (xi) SEQUENCE DESCRIPTION: SEQ ID NO:16:

AAGGGCTTCT TCCTTA 16

(2) INFORMATION FOR SEQ ID NO:17:

(i) SEQUENCE CHARACTERISTICS:
(A) LENGTH: 20 Nucleotides
(B) TYPE: nucleic acid
(C) STRANDEDNESS: single stranded
(D) TOPOLOGY: linear (xi) SEQUENCE DESCRIPTION: SEQ ID NO:17:

TGAAGGGCTT CTTCCTTATT 20

(2) INFORMATION FOR SEQ ID NO:18:

(i) SEQUENCE CHARACTERISTICS:
(A) LENGTH: 22 Nucleotides
(B) TYPE: nucleic acid
(C) STRANDEDNESS: single stranded
(D) TOPOLOGY: linear (xi) SEQUENCE DESCRIPTION: SEQ ID NO:18:

CTGAAGGGCT TCTTCCTTAT TG 22

(2) INFORMATION FOR SEQ ID NO:19:

(i) SEQUENCE CHARACTERISTICS:
(A) LENGTH: 14 Nucleotides
(B) TYPE: nucleic acid
(C) STRANDEDNESS: single stranded
(D) TOPOLOGY: linear (xi) SEQUENCE DESCRIPTION: SEQ ID NO:19:

AGGGCTTTTG AACT 14

(2) INFORMATION FOR SEQ ID NO:20:

(i) SEQUENCE CHARACTERISTICS:
(A) LENGTH: 16 Nucleotides
(B) TYPE: nucleic acid
(C) STRANDEDNESS: single stranded
(D) TOPOLOGY: linear (xi) SEQUENCE DESCRIPTION: SEQ ID NO:20:

AAGGGCTTTT GAACTC 16

(2) INFORMATION FOR SEQ ID NO:21:

(i) SEQUENCE CHARACTERISTICS:
(A) LENGTH: 20 Nucleotides
(B) TYPE: nucleic acid
(C) STRANDEDNESS: single stranded ( D ) TOPOLOGY: linear ( x i ) SEQUENCE DESCRIPTION: SEQ ID NO:21:

TGAAGGGCTT TTGAACTCTG 20

( 2 ) INFORMATION FOR SEQ ID NO:22:

( i ) SEQUENCE CHARACTERISTICS:
( A ) LENGTH: 22 Nucleotides
( B ) TYPE: nucleic acid
( C ) STRANDEDNESS: single stranded
( D ) TOPOLOGY: linear ( x i ) SEQUENCE DESCRIPTION: SEQ ID NO:22:

CTGAAGGGCT TTTGAACTCT GC 22

( 2 ) INFORMATION FOR SEQ ID NO:23:

( i ) SEQUENCE CHARACTERISTICS:
( A ) LENGTH: 14 Nucleotides
( B ) TYPE: nucleic acid
( C ) STRANDEDNESS: single stranded
( D ) TOPOLOGY: linear ( x i ) SEQUENCE DESCRIPTION: SEQ ID NO:23:

AGGGCTTCTG CGTC 14

( 2 ) INFORMATION FOR SEQ ID NO:24:

( i ) SEQUENCE CHARACTERISTICS:
( A ) LENGTH: 16 Nucleotides
( B ) TYPE: nucleic acid
( C ) STRANDEDNESS: single stranded
( D ) TOPOLOGY: linear ( x i ) SEQUENCE DESCRIPTION: SEQ ID NO:24:

AAGGGCTTCT GCGTCT 16

( 2 ) INFORMATION FOR SEQ ID NO:25:

( i ) SEQUENCE CHARACTERISTICS:
( A ) LENGTH: 20 Nucleotides
( B ) TYPE: nucleic acid
( C ) STRANDEDNESS: single stranded
( D ) TOPOLOGY: linear ( x i ) SEQUENCE DESCRIPTION: SEQ ID NO:25:

TGAAGGGCTT CTGCGTCTCC 20

( 2 ) INFORMATION FOR SEQ ID NO:26:

( i ) SEQUENCE CHARACTERISTICS:
( A ) LENGTH: 22 Nucleotides
( B ) TYPE: nucleic acid
( C ) STRANDEDNESS: single stranded
( D ) TOPOLOGY: linear ( x i ) SEQUENCE DESCRIPTION: SEQ ID NO:26:

CTGAAGGGCT TCTGCGTCTC CA 22

( 2 ) INFORMATION FOR SEQ ID NO:27:

( i ) SEQUENCE CHARACTERISTICS:
( A ) LENGTH: 18 Nucleotides
( B ) TYPE: nucleic acid
( C ) STRANDEDNESS: single stranded
( D ) TOPOLOGY: linear ( x i ) SEQUENCE DESCRIPTION: SEQ ID NO:27:

TACTGGCCGC TGAAGGGC 18

( 2 ) INFORMATION FOR SEQ ID NO:28:

( i ) SEQUENCE CHARACTERISTICS:
( A ) LENGTH: 24 Nucleotides
( B ) TYPE: nucleic acid
( C ) STRANDEDNESS: single stranded
( D ) TOPOLOGY: linear ( x i ) SEQUENCE DESCRIPTION: SEQ ID NO:28:

GCTGAAGGGC TTCTTCCTTA TTGA 24

( 2 ) INFORMATION FOR SEQ ID NO:29:

( i ) SEQUENCE CHARACTERISTICS:
( A ) LENGTH: 26 Nucleotides
( B ) TYPE: nucleic acid
( C ) STRANDEDNESS: single stranded
( D ) TOPOLOGY: linear ( x i ) SEQUENCE DESCRIPTION: SEQ ID NO:29:

CGCTGAAGGG CTTCTTCCTT ATTGAT 26

( 2 ) INFORMATION FOR SEQ ID NO:30:

( i ) SEQUENCE CHARACTERISTICS:
( A ) LENGTH: 24 Nucleotides
( B ) TYPE: nucleic acid
( C ) STRANDEDNESS: single stranded
( D ) TOPOLOGY: linear ( x i ) SEQUENCE DESCRIPTION: SEQ ID NO:30:

GCTGAAGGGC TTTTGAACTC TGCT 24

( 2 ) INFORMATION FOR SEQ ID NO:31:

( i ) SEQUENCE CHARACTERISTICS:
( A ) LENGTH: 26 Nucleotides
( B ) TYPE: nucleic acid
( C ) STRANDEDNESS: single stranded
( D ) TOPOLOGY: linear ( x i ) SEQUENCE DESCRIPTION: SEQ ID NO:31:

CGCTGAAGGG CTTTTGAACT CTGCTT 26

( 2 ) INFORMATION FOR SEQ ID NO:32:

( i ) SEQUENCE CHARACTERISTICS:
( A ) LENGTH: 24 Nucleotides
( B ) TYPE: nucleic acid
( C ) STRANDEDNESS: single stranded
( D ) TOPOLOGY: linear ( x i ) SEQUENCE DESCRIPTION: SEQ ID NO:32:

GCTGAAGGGC TTCTGCGTCT CCAT 24

( 2 ) INFORMATION FOR SEQ ID NO:33:

( i ) SEQUENCE CHARACTERISTICS:
( A ) LENGTH: 26 Nucleotides
( B ) TYPE: nucleic acid
( C ) STRANDEDNESS: single stranded
( D ) TOPOLOGY: linear ( x i ) SEQUENCE DESCRIPTION: SEQ ID NO:33:

```
CGCTGAAGGG CTTCTGCGTC TCCATG    26
```

( 2 ) INFORMATION FOR SEQ ID NO:34:

( i ) SEQUENCE CHARACTERISTICS:
      ( A ) LENGTH: 23 Nucleotides
      ( B ) TYPE: nucleic acid
      ( C ) STRANDEDNESS: single stranded
      ( D ) TOPOLOGY: linear ( x i ) SEQUENCE DESCRIPTION: SEQ ID NO:34:

```
ATCAATAAGG AAGCCCTTCA GCG    23
```

SELECTIVE INHIBITION OF LEUKEMIC CELL PROLIFERATION BY BCR-ABL ANTISENSE OLIGONUCLEOTIDES

CROSS REFERENCE TO RELATED APPLICATION

This is a continuation of patent application Ser. No. 07/869,911, filed Apr. 14, 1992, now abandoned which is a continuation-in-part of patent application Ser. No. 07/718, 302 filed Jun. 18, 1991, now abandoned.

REFERENCE TO GOVERNMENT GRANT

The invention described herein was supported in part by National Institutes of Health grants CA46782 and CA36896.

FIELD OF THE INVENTION

The invention relates to antisense oligonucleotides complementary to mRNA and therapeutic uses thereof. In particular, the invention relates to such antisense oligonucleotides complementary to the bcr-abl junction, and the use thereof in treatment of leukemias characterized by the Philadelphia chromosome translocation.

BACKGROUND OF THE INVENTION

Chronic myelogenous leukemia, sometimes referred to as chronic myeloid leukemia (CML), was the first neoplastic disease to be associated with a specific chromosomal abnormality, namely the Philadelphia or $Ph^1$ chromosome. At the molecular level, the most notable feature is the translocation of the proto-oncogene c-abl from the long arm of chromosome 9 to the breakpoint cluster region (bcr) on chromosome 22, resulting in the formation of bcr-abl hybrid genes. The break occurs near the end of the long arm of chromosome 9 (band 9q34) and in the upper half of chromosome 22 (band 22q11).

The c-abl proto-oncogene normally encodes a protein with tyrosine kinase activity. This activity is augmented in cells carrying bcr-abl hybrid genes. The gene located at the breakpoint on chromosome 22 is called bcr because the break in chromosome 22 in CML occurs in a very small 5.8-kilobase (kb) segment (breakpoint cluster region) of the gene on chromosome 22. For purposes herein, BCR refers to the entire gene encompassing the breakpoint cluster region, while bcr shall refer to the 5.8-kb segment that is the region of the break in CML. The BCR gene is a relatively large gene of about 130 kb.

Cloning of the c-abl gene has revealed that it spans at least 230kb, and contains at least 11 exons. Two alternative first exons exist, namely exon 1a and exon 1b, which are spliced to the common splice acceptor site, exon 2. Exon 1a is 19 kb proximal to exon 2. Exon 1b, which is somewhat smaller than exon 1a, is more than 200 kb proximal to exon 2. As a result of this configuration, at least two major c-abl messages are transcribed, differing in their 5' regions. (Shtivelman et al., *Cell* 47, 277 (1986); Bernards et al., *Mol. Cell. Biol.* 7, 3231 (1987); Fainstein et al., *Oncogene* 4, 1477–1481 (1989)). If exon 1b is used, the mRNA is 7.0 kb. If exon 1a is used, the mRNA is 6.0 kb. Each of exons 1a and 1b are preceded by a transcriptional promotor.

The 6-kb c-abl transcript consists of exons 1a through 11. The 7-kb transcript begins with exon 1b, skips the 200 kb distance to exon 2, omits exon 1a, and joins to exons 2 through 11. Thus, both c-abl messages share a common set of 3' exons, starting from the c-abl exon 2. Consequently, the messages code for two proteins that share most of their amino acid sequence, except for the N-termini. Since the coding begins with the first exon, exonic selection will determine the protein product. The 9;22 translocation in CML results in the abnormal juxtaposition of abl sequences adjacent to bcr sequences.

The entire BCR gene has been mapped (Heisterkamp et al., *Nature* 315, 758 (1985)). The fusion of the BCR gene with c-abl leads to an 8.5 kb chimeric mRNA consisting of 5' BCR sequences and 3' abl sequences. The chimeric message is in turn translated into a larger chimeric abl protein (210 kDa) that has increased tyrosine kinase activity (Konopka et al., *Cell* 37, 1035 (1984); Kloetzer et al., *Virology* 140, 230 (1985); Konopka et al., *Proc. Natl. Acad. Sci. U.S.A.* 82, 1810 (1985)). The 210 kDa protein is considerably larger than the normal human abl protein of 145 kDa, and has a very high tyrosine kinase activity.

Two major types of bcr-abl translocations are known, characterized by two different bcr-abl junctions. One translocation is between bcr exon 2 and abl exon 2, while another translocation is between bcr exon 3 and the same abl exon 2 (Shtivelman et al., *Cell* 47, 277–284 (1986)). The two types of junction have been referred to as the "L-6" (or "b2a2") and "K-28" (or "b3a2") junctions, respectively. The alternative splicing from two bcr-abl exons to the abl coding sequence results in two different bcr-abl fusion proteins, one including the 25 amino acids encoded by bcr exon 3 and one which lacks those amino acids. One or both of these junctions is detected in $Ph^1$-positive CML patients (Shtivelman et al., *Blood* 69, 971 (1986)).

A significant portion of acute lymphocytic leukemia (ALL) patients carry $Ph^1$ chromosomes in their leukemic cells. $Ph^1$-positive ALL is generally regarded as being less responsive to chemotherapeutic treatment than $Ph^1$-negative forms of ALL. This is particularly true of children with $Ph^1$-positive ALL.

Approximately one half of $Ph^1$-positive individuals afflicted with ALL express either of the two major bcr-abl junctions, L-6 or K-28. The remainder have bcr-abl genes characterized by a junction formed by the fusion of bcr exon 1 and c-abl exon 2 ("b1a2" junction). See Fainstein et al., *Nature* 330, 386–388 (1987).

There are thus at least three distinct bcr-abl mRNAs. The 3 mRNAs contain one of three different bcr exons fused to the same abl exon. About one half of CML patients have the b2a2 junction, while the other half are characterized by the b3a2 junction. ALL patients are about fifty percent b1a2, twenty-five percent b2a2 and twenty-five percent b3a2. An improved polymerase chain reaction (PCR) procedure has been proposed for distinguishing among the three types of molecular defects using analyses of PCR reaction products by hybridization with probes specific for the three known bcr-abl fusion sequences (Kawasaki et al., *Prod. Anal. Acad. Sci. U.S.A.* 85, 5698–5702 (1988)). Clinically, CML invariably progresses from the chronic phase into the blast crisis. In chronic phase CML, the increase in mature and immature myeloid elements in bone marrow and peripheral blood is the most characteristic feature (Koeffler et al., *N. Engl. J. Med.* 304, 201 (1981)). Kinetic studies indicate that these abnormal cells do not proliferate or mature faster than their normal counterparts. Instead, the basic defect underlying the exuberant granulopoiesis in CML appears to reside in the expansion of the myeloid progenitor cell pool in bone marrow and peripheral blood. *Id.* Nevertheless, the generation of terminally differentiated cells indicates that the process of hematopoiesis retains some normal features. In contrast, during blastic transformation, the leukemic cells exhibit a marked degree of differentiation arrest with a "blast" phenotype (Rosenthal et al., *Am. J. Med.* 63, 542 (1977)). The onset of the blastic transformation or "blast crisis" limits the therapeutic options available. The disease-free period, and consequently survival, is generally brief. Typically it is less than about four months.

The earliest treatment of CML chronic phase consisted of chemotherapy with an alkylating agent such as busulfan, and inhibitors of DNA synthesis, such as hydroxyurea. While both drugs are useful in the control of the excessive granulopoiesis of CML, their effect is not specific, since they inhibit nucleic acid synthesis in both normal and leukemic cells. With this standard approach to treatment, the median survival is about 47 months, but there is little evidence that these patients live significantly longer than patients who receive no therapy (Bergsheel, "Chronic Granulocytic Leukemia", in *Fairbanks* (ed.) *Current Hemotology*, Vol. 2, Wiley, New York, pp. 1–26 (1983)). Attempts to eliminate the leukemic clone by splenic irradiation, splenectomy and intensive chemotherapy have been observed to suppress the $Ph^1$-chromosome-positive population temporarily in one third of CML patients, but failed to alter the course of the disease (Cunningham et al., *Blood* 53, 375 (1975)). The leukemic population always recurred, resulting ultimately in blast crisis and death.

Chemotherapeutic agents such as busulfan and hydroxyurea are not specific since they inhibit nucleic acid synthesis both in normal and leukemic cells. Moreover, it is debatable whether they are .effective in altering or delaying the natural course of the disease.

More recently, interferons were added to the therapeutic armamentarium in CML chronic phase. Alpha-interferon (3–9 million units intramuscularly each day) produces a normalization of the blood count in about three quarters of chronic phase CML patients. Unlike patients treated with hydroxyurea and busulfan, more than one third of alpha-interferon treated patients have a decrease in $Ph^1$-chromosome-containing methaphases, and about 15% of treated patients have fewer than 5% $Ph^1$-positive cells. The experience with alpha-interferon is limited, since it was initially utilized in 1985. There is yet no firm evidence that the prognosis is better in interferon-treated patients than in those treated with hydroxyurea or busulfan. In addition, alpha-interferon has several side effects that include fever, anorexia, muscle and bone pain, depression, and often immune thrombocytopenia. A further disadvantage of alpha-interferon is that it is more complex to administer in comparison to hydroxyurea or busulfan (intramuscular injection versus oral intake). Although alpha-interferon preferentially affects the growth of the leukemic clone, the effect is, however, non-specific, as indicated by the persistence of $Ph^1$ leukemic cells and the inhibition of normal hematopoietic cell growth.

In addition to chemotherapy and alpha-interferon treatment, a more rigorous therapy for CML involves marrow transplantation during chronic phase in patients who have an identical twin, a histocompatible sibling, or access to a histocompatible unrelated donor. Marrow transplantation is typically carried out following extensive chemotherapy and total body radiation to eradicate $Ph^1$-positive leukemia cells. There is generally a long-term survival in 45–70% of patients following marrow transplantation, however, there is a 20–40% post-transplantation mortality. Marrow transplantation is most successful if carried out early in the course of the chronic phase of the disease. About 40% of patients transplanted during the chronic phase achieve long-term survival beyond five years, free of leukemia and the $Ph^1$ chromosome (Bergsheel, *J. Cancer Res. Clin. Oncol.* 116, 104–105 (1990)). Transplants during the "accelerated" or blast phases are less successful. Less than 10% of such patients survive beyond five years free of leukemia (Id.) The "accelerated" phase precedes blast transformation, and is usually characterized by a progressive loss of the capability of the leukemic clone to differentiate in mature end cells.

Autologous marrow infusion has been increasingly used in CML patients, especially those in the accelerated phase. In preparation for autologous marrow infusion, marrow cells are harvested from the affected individual, are "purged" of leukemia cells by chemical agents, and returned to the patient following extensive chemotherapy or total body radiation.

During "blast crisis", therapy is for the most part ineffective, and the disease is fatal, within at most 3–6 months. While treatments such as alpha-interferon and autologous marrow infusion are promising, they are non-specific. What is needed is a $Ph^1$-specific agent which selectively targets cells expressing the Philadelphia chromosome while leaving other cells intact.

Caracciolo et al., *Science* 245, 11007–1110 (1989) disclose inhibition of the $Ph^1$-positive cell line K562 utilizing the antisense oligodeoxynucleotide TACTGGCCGC TGAAGGGC (SEQ ID NO:27) which is complementary to 18 nucleotides of the second exon of c-abl. Cells of the K562 line have the b2a2 junction. While the aforesaid antisense oligomer was demonstrated effective in reducing bcr-abl protein levels, the oligomer is not specific for the bcr-abl junction, as it also hybridizes to the message from untranslocated abl.

Recently, mice infected with a defective virus carrying human bcr-abl genes have been shown to develop a CML-like syndrome (Daley et al., *Science* 247, 824–830 (1990); Heislerkamp et al., *Nature* 344, 251–253 (1990)). However, such studies utilizing artificial bcr-abl constructs to initiate a CML-like condition in transgenic animals do not indicate whether bcr-abl expression is necessary for maintenance of the established disease state, or whether inhibition of bcr-abl expression may have an impact on the disease state.

SUMMARY OF THE INVENTION

A method for treating a $Ph^1$-positive leukemia is provided. RNA transcribed from a hybrid bcr-abl gene is extracted from cells isolated from a $Ph^1$-positive leukemia-afflicted individual. The nucleotide sequence of the region of the bcr-abl mRNA transcript surrounding the bcr-abl translocation junction is determined. An about 13-mer to about 26-mer antisense oligonucleotide is then prepared having a nucleotide sequence complementary to a target sequence of the bcr-abl mRNA transcript, which target sequence includes the bcr-abl translocation junction and not more than about 13 nucleotides of the abl-derived portion of the transcript. The antisense oligonucleotide is hybridizable to the target sequence. An effective amount of the antisense oligonucleotide is administered to the afflicted individual or to cells harvested therefrom.

Preferably, the oligonucleotide is from a 15-mer to a 21-mer, that is, an oligomer containing 15 to 21 nucleotides. More preferably, the oligonucleotide is from a 15-mer to an 18-mer. The oligonucleotide is preferably an oligodeoxynucleotide. According to one preferred embodiment, the oligonucleotide comprises a phosphorothioate oligodeoxynucleotide.

Typically, the antisense oligonucleotide will not contain more than one nucleotide mismatch with respect to the bcr-abl mRNA target sequence to which it hybridizes. Preferably, the antisense oligonucleotide and target sequence are completely complementary, that is, there are no mismatches.

The bcr-abl mRNA target sequence to which the oligonucleotide hybridizes preferably comprises from about 6 to about 13 abl-derived nucleotides, the balance of said target sequence comprising bcr-derived nucleotides. According to a preferred embodiment, the bcr-abl mRNA target sequence comprises an about equal number of abl-derived nucleotides and bcr-derived nucleotides.

One method of treatment comprises treating bone marrow cells aspirated from the $Ph^1$-leukemia afflicted individual with antisense oligonucleotide, and returning the thus-treated cells to the body of the afflicted individual.

The invention further provides a pharmaceutical composition for treating $Ph^1$-positive leukemia comprising a pharmaceutical carrier and an about 13-mer to about 26-mer antisense oligonucleotide having a nucleotide sequence complementary to a target sequence of the mRNA transcript of the human bcr-abl gene, which target sequence includes the bcr-abl translocation junction and not more than about 13 nucleotides of the abl-derived portion of the transcript, the oligonucleotide being hybridizable to the target sequence.

As used in the herein specification and appended claims, unless otherwise indicated, the term "oligonucleotide" includes both oligomers of ribonucleotide, i.e., oligoribonucleotides, and oligomers of deoxyribonucleotide, i.e., oligodeoxyribonucleotides (also referred to herein as "oligodeoxynucleotides"). Oligodeoxynucleotides are preferred.

As used herein, unless otherwise indicated, the term "oligonucleotide" also includes oligomers which may be large enough to be termed "polynucleotides".

The terms "oligonucleotide" and "oligodeoxynucleotide" include not only oligomers and polymers of the common biologically significant nucleotides, i.e., the nucleotides adenine ("A"), deoxyadenine ("dA"), guanine ("G"), deoxyguanine ("dG"), cytosine ("C"), deoxycytosine ("dC"), thymine ("T") and uracil ("U"), but also include oligomers and polymers hybridizable to the c-myb mRNA transcript which may contain other nucleotides. Likewise, the terms "oligonucleotide" and "oligodeoxynucleotide" may include oligomers and polymers wherein one or more purine or pyrimidine moieties, sugar moieties or internucleotide linkages is chemically modified. The term "oligonucleotide" is thus understood to also include oligomers which may properly be designated as "oligonucleosides" because of modification of the internucleotide phosphodiester bond. Such modified oligonucleotides include, for example, the alkylphosphonate oligonucleosides, discussed below.

The term "phosphorothioate oligonucleotide" means an oligonucleotide wherein one or more of the internucleotide linkages is a phosphorothioate group,

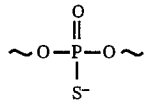

as opposed to the phosphodiester group

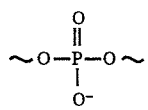

which is characteristic of unmodified oligonucleotides.

By "alkylphosphonate oligonucleoside" is meant an oligonucleotide wherein one or more of the internucleotide linkages is an alkylphosphonate group,

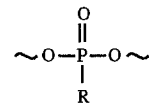

where R is an alkyl group preferably methyl or ethyl.

The term "downstream" when used in reference to a direction along a nucleotide sequence means the 5'→3' direction. Similarly, the term "upstream" means the 3'→5' direction. Unless otherwise indicated, nucleotide sequences appearing herein are written from left to right in the 5'→3' direction.

The term "bcr-abl mRNA transcript" means any mRNA transcript of the human bcr-abl gene, including all variation of the bcr-abl gene, such as the hybrid genes formed from the translocation between bcr exon 2 and c-abl-exon 2 ("b2a2"), the translocation between bcr exon 3 and c-abl exon 2 ("b3a2"), and between bcr exon 1 and c-abl exon 2 ("b1a2").

DESCRIPTION OF THE FIGURES

FIG. 1 comprises the cDNA nucleotide sequence (SEQ ID NO:1) around the bcr-abl junction derived from a group of five CML patients in blast crisis. The arrow indicates the bcr-abl breakpoint, and the box delineates an 18-nucleotide target sequence corresponding to the breakpoint junction. The bcr-derived portion of the sequence lies upstream from the breakpoint. The sequence is that of the L-6 type junction, formed by fusion of bcr exon 2 to c-abl exon 2.

FIG. 3 comprises the cDNA nucleotide sequence (SEQ ID NO:4) around the bcr-abl junction derived from two CML patients in blast crisis. The arrow indicates the bcr-abl breakpoint, and the box delineates an 18-nucleotide target sequence corresponding to the breakpoint junction. The bcr-derived portion of the sequence lies upstream from the breakpoint. The sequence is that of the K-28 type bcr-abl junction, formed by fusion of bcr exon 3 to c-abl exon 2.

FIG. 5 comprises the cDNA nucleotide sequence (SEQ ID NO:7) around the bcr-abl junction derived from cells of a $Ph^1$-positive cell line. The arrow indicates the bcr-abl breakpoint, and the box delineates an 18-nucleotide target sequence corresponding to the breakpoint junction. The bcr-derived portion of the sequence lies upstream from the breakpoint. The junction is formed by fusion of bcr exon 1 to c-abl exon 2.

DETAILED DESCRIPTION OF THE INVENTION

Figure 2A:
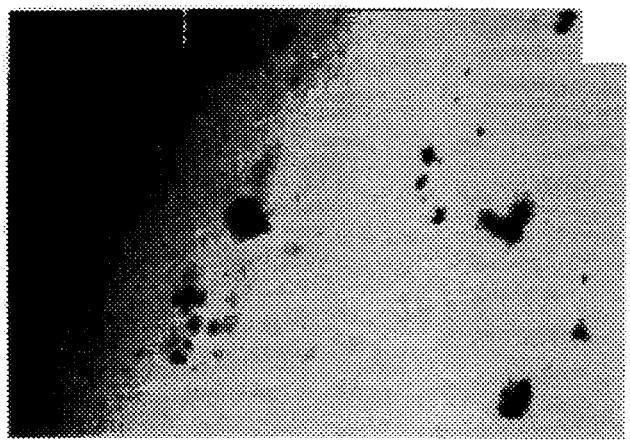
FIGS. 2A, 2B and 2C comprise photographs of 10-day CML cell cultures containing blast crisis patient cells which were untreated (FIG. 2A); treated in vitro with an 18-mer antisense oligonucleotide (SEQ ID NO:2) complementary to the target sequence of FIG. 1, but containing four nucleotide mismatches (FIG. 2B); or treated with an 18-mer antisense oligonucleotide (SEQ ID NO:3) completely complementary to the same target sequence (FIG. 2C).

We have found that expression of the hybrid bcr-abl gene is necessary for the maintenance of the leukemic disease state in Ph$^1$-positive leukemias. The proliferation of leukemic cells may be effectively inhibited by administration of therapeutic "antisense" oligonucleotides which specifically hybridize to a target sequences in a region of the bcr-abl mRNA transcript corresponding to the bcr-abl translocation junction. The therapeutic oligonucleotides are selected so as to have a nucleotide sequence complementary to the target sequence. Even leukemic cells from patients in blast crisis may be inhibited. This is surprising since by the time the disease has progressed to the acute stage, a variety of genetic abberations, including additional translocations, have occurred, in addition to the bcr-abl translocation.

There is considerable individual variation in the nucleotide sequence of the bcr-abl junction. At least three major translocation types are presently known (b2a2, b3a2 and b1a2). Effective antisense treatment requires closely matching a target sequence of the individual patient's bcr-abl junction with a complementary antisense oligonucleotide. The present invention therefore provides a method of treatment utilizing antisense oligonucleotides having a sequence complementary to the specific nucleotide sequence of the individual patient's bcr-abl junction. Such oligonucleotides selectively inhibit only cells expressing the hybrid bcr-abl gene, the result is a patient-specific, malignant cell-specific therapeutic method for treating Ph$^1$-positive leukemias. While conventional chemotherapy inhibits nucleic acid synthesis in both normal and leukemic cells, only leukemic cells which express the hybrid bcr-abl gene are affected. Selection of appropriate dosages in administering oligomer according to the present invention is therefore less critical than in the case of conventional chemotherapy.

Because of the heterogeneity in the nucleotide sequence surrounding the bcr-abl breakpoint junction, therapy involves first sequencing the individual patient's junction, and thereafter administering an oligonucleotide which is preferably completely complementary to that specific junction. In this manner, the likelihood of complete hybridization to the bcr-abl transcript, and the halt of bcr-abl translation, is maximized. Substantial inhibition of Ph$^1$-positive cell proliferation is obtained.

The therapeutic antisense oligonucleotide is prepared such that it hybridizes to a target sequence in the bcr-abl gene mRNA transcript which includes the specific bcr-abl breakpoint junction. The antisense oligonucleotide is further selected such that it is complementary to such a target sequence including not more than about 13 oligonucleotides of the abl-derived portion of the transcript. By "abl-derived portion" is meant that portion of the bcr-abl RNA transcript which results from the transcription of the abl coding sequence which is translocated to the bcr coding sequence in the chromosomal translocation event giving rise to formation of the Ph$^1$ chromosome. Similarly, by "bcr-derived portion" of the bcr-abl transcript is meant that portion which results from the transcription of the bcr coding sequence which is juxtaposed to c-abl.

The c-abl gene is expressed in normal cells and plays a critical role in regulating normal hematopoiesis. Thus, as we have shown previously, antisense oligonucleotides complementary to and hybridizable with the human c-abl mRNA transcript inhibit myelopoiesis, but do so at a concentration that spares erythropoiesis. While antisense oligonucleotides hybridizable to c-abl mRNA are thus useful in treating disorders characterized by abnormal proliferation of myeloid origin cells, such is not the primary object of the present invention. Rather, it is the object of the present invention to fashion and administer to an afflicted individual antisense oligonucleotides which specifically hybridize to the bcr-abl junction without substantially cross-hybridizing to untranslocated c-abl sequences. Thus, the present invention avoids impairment of normal c-abl function by selecting antisense oligonucleotides which hybridize to no more than about 13 nucleotides of the c-abl-derived portion of the bcr-abl transcript. Antisense oligonucleotides hybridizable to a region of the bcr-abl transcript, including the translocation breakpoint junction and extending no more than 13 nucleotides into the abl-derived portion, will only minimally, if at all, cross-hybridize to the untranslocated c-abl message of normal, non-leukemic hematopoietic cells. In this manner, Ph$^1$ leukemic cell proliferation is inhibited without adverse consequence to normal hematopoiesis.

On the other hand, a somewhat greater degree of non-specific-hybridization of antisense oligonucleotides to transcripts from untranslocated bcr genes may be tolerated, since expression of the bcr gene is presently not regarded as important for normal hematopoiesis. However, substantial cross-hybridization to untranslocated bcr should nonetheless be avoided, since cell types other than hematopoietic cells may require bcr expression for normal cell function.

In order to ensure specific hybridization of the therapeutic antisense oligonucleotide to bcr-abl transcripts, it is preferred that the oligonucleotide has a sequence including from about 6 to about 13 abl-derived nucleotides, the balance of the antisense oligonucleotide being complementary to bcr-derived nucleotides of the target sequence. Most preferably, the antisense molecule is complementary to a target mRNA sequence containing an about equal number of abl-derived nucleotides and bcr-derived nucleotides, that is, an about equal number of nucleotides on either side flanking the translocation breakpoint. Accordingly, one group of most preferred antisense oligonucleotides complementary to the b2a2 junction includes the following even-numbered 14 through 26-mers:

| breakpoint ↓ | |
|---|---|
| AGGGCTT CTTCCTT | (SEQ ID NO: 15) |
| AAGGGCTT CTTCCTTA | (SEQ ID NO: 16) |
| GAAGGGCTT CTTCCTTAT | (SEQ ID NO: 3) |
| TGAAGGGCTT CTTCCTTATT | (SEQ ID NO: 17) |
| CTGAAGGGCTT CTTCCTTATTG | (SEQ ID NO: 18) |
| GCTGAAGGGCTT CTTCCTTATTGA | (SEQ ID NO: 28) |
| CGCTGAAGGGCTT CTTCCTTATTGAT | (SEQ ID NO: 29) |

Correspondingly, the following even-numbered 14- through 26-mers comprise most preferred antisense oligonucleotides complementary to, respectively, the b3a2 junction,

| breakpoint ↓ | |
|---|---|
| AGGGCTT TTGAACT | (SEQ ID NO: 19) |
| AAGGGCTT TTGAACTC | (SEQ ID NO: 20) |
| GAAGGGCTT TTGAACTCT | (SEQ ID NO: 6) |
| TGAAGGGCTT TTGAACTCTG | (SEQ ID NO: 21) |
| CTGAAGGGCTT TTGAACTCTGC | (SEQ ID NO: 22) |
| GCTGAAGGGCTT TTGAACTCTGCT | (SEQ ID NO: 30) |
| CGCTGAAGGGCTT TTGAA&TCTGCTT | (SEQ ID NO: 31) | and the b1a2 junction:

| breakpoint ↓ | |
|---|---|
| AGGGCTT CTGCGTC | (SEQ ID NO: 23) |
| AAGGGCTT CTGCGTCT | (SEQ ID NO: 24) |
| GAAGGGCTT CTGCGTCTC | (SEQ ID NO: 9) |
| TGAAGGGCTT CTGCGTCTCC | (SEQ ID NO: 25) |
| CTGAAGGGCTT CTGCGTCTCCA | (SEQ ID NO: 26) |
| GCTGAAGGGCTT CTGCGTCTCCAT | (SEQ ID NO: 32) |
| CGCTGAAGGGCTT CTGCGTCTCCATG | (SEQ ID NO: 33) |

The initial step in the therapeutic method of the invention is the identification of the patient-to-be-treated as possessing the hybrid bcr-abl gene. This may be accomplished by probing the patient RNA or cDNA with suitably labeled nucleic acid probes for bcr-abl, such as those disclosed in U.S. Pat. Nos. 4,681,840 and 4,874,853, the entire disclosures of which are incorporated herein by reference. Total RNA may be probed with one or more of the above-listed antisense oligonucleotides. Finally, molecular diagnosis of $Ph^1$-positive leukemias could be achieved by amplification and detection of characteristic mRNA sequences utilizing a reverse transcriptase polymerase chain reaction (RT-PCR) procedure, such as the procedure disclosed by Kawasaki et al., *Proc. Natl. Acad. Sci. U.S.A.*, 85, 5698–5702 (1988), incorporated herein by reference.

Upon diagnosis establishing the presence of the bcr-abl gene, leukemic $Ph^1$-positive cells are obtained from the peripheral blood and/or bone marrow of the patient for sequencing of the bcr-abl junction. The cells may be enriched by procedures such as Ficoll-Hipaque centrifugation to remove non-mononuclear cells. RNA containing the nucleotide sequence corresponding to the bcr-abl hybrid gene is extracted for reverse transcription, amplification and sequencing. Preferably, the source of bcr-abl nucleotide sequence information comprises RNA.

Accordingly, total mRNA is isolated from the $Ph^1$-positive enriched cells according to well-known extraction procedures, such as the procedures described in *Molecular Cloning: A Laboratory Manual* (2d. ed. 1989), J. Sambrook et al, eds., pp. 7.9–7.11, incorporated herein by reference. In particular, a single step RNA isolation method may be utilized, such as the acid guanidinium thiocyanate-phenol-chloroform-extraction method described by Chomzcynski et al., *Anal. Biochem.* 162, 156–159 (1987), incorporated herein by reference. The bcr-abl junction is thereafter cloned by any of the known amplification techniques, most preferably by RT-PCR. Accordingly, synthetic primers specific for bcr exon 2 and abl exon 2 are utilized in a RT-PCR technique to clone the b2a2 junction. Similarly, synthetic primers specific for bcr exon 3 and abl exon 2 are utilized for amplifying the b3a2 junction. Such synthetic primers may be prepared based upon the published sequences for the b2a2 and b3a2 breakpoint junctions (Shtivelman et al., *Cell* 47, 277–286 (1986), incorporated herein by reference, and Fainstein et al., *Nature* 330, 386–388 (1987), incorporated herein by reference).

Following the amplification step, the polymerase chain reaction product may be sequenced directly. Alternatively, the product may be further amplified by cloning in a suitable vector, e.g., the BLUESCRIPT SK (M13-) vector (Stratagene Cloning Systems, La Jolla, Calif.), which is described in *Molecular Cloning*, p. 1.20 and Short et al., *Nucleic Acids Res.* 16, 7583 (1988). Sequencing of the relevant region around the bcr-abl breakpoint of the cloned polymerase chain reaction product is then carried out according to conventional sequencing procedures, such as described in *Molecular Cloning*, chapter 13, incorporated by reference.

Antisense oligonucleotides having a sequence complementary to the relevant bcr-abl breakpoint of the individual patient are then prepared, based upon the sequence information obtained. In general, the antisense oligonucleotide will have a sequence which is completely complementary to the target sequence of the bcr-abl message. Absolute complementarity is not, however, required, particularly in larger oligomers. Thus, unless otherwise indicated, reference herein to a "nucleotide sequence complementary to a target sequence" does not necessarily mean a sequence having 100% complementarity with the transcript. In general, any oligonucleotide having sufficient complementarity to form a stable duplex with the target region of the bcr-abl message is suitable. Stable duplex formation depends on the sequence and length of the hybridizing oligonucleotide and the degree of complementarity with the target region of the message. Generally, the larger the hybridizing oligomer, the more mismatches may be tolerated. More than one mismatch would probably not be tolerated for antisense oligomers of less than about 18–21 nucleotides. One skilled in the art may readily determine the degree of mismatching which may be tolerated between any given antisense oligomer and the bcr-abl message target sequence, based upon the melting point, and therefore the stability of the resulting duplex. Melting points of duplexes of a given base pair composition can be determined from standard texts, such as *Molecular Cloning: A Laboratory Manual,* (2nd ed., 1989, J. Sambrook et al., eds.) Even so, not more than one mismatch is preferred in oligonucleotides greater than 18–21 nucleotides long. Oligonucleotides of 17 or less nucleotides are preferably completely complementary to the target sequence. Most preferably, the oligonucleotides administered according to the present invention will have 100% complementarity with the target sequence, regardless of oligonucleotide size.

Antisense oligonucleotides shorter than about 13 nucleotides may be less specific in hybridizing to the target bcr-abl mRNA sequence, may be more readily destroyed by enzymatic digestion, and may be destabilized by enzymatic digestion. Hence, oligonucleotides having 12 or fewer nucleotides are not recommended in the practice of the present invention. Sequences longer than about 26 nucleotides may be somewhat less effective in inhibiting bcr-abl translation because of decreased uptake by the target cell. Furthermore, the larger the oligomer becomes, the more opportunity for non-specific hybridization with either untranslocated bcr sequences or untranslocated c-abl sequences. Thus, the present invention utilizes oligonucleotides containing from about 13 to about 26 nucleotides, preferably from about 15 to about 21 nucleotides, most preferably from about 15 to about 18 nucleotides.

The antisense oligonucleotides utilized in the practice of the present invention may be synthesized by any of the known chemical oligonucleotide synthesis methods. Such methods are generally described, for example, in Winnacker, *From Genes to Clones: Introduction to Gene Technology,* VCH Verlagsgesellschaft m.b.H. (Ibelgaufts Trans. 1987). The oligonucleotides are most advantageously prepared by utilizing any of the commercially available automated nucleic acid synthesizers. One such device, the 380B DNA synthesizer model of Applied Biosystems (Foster City, Calif.), utilizes β-cyanoethyl phosphoramidite chemistry.

The oligonucleotide employed may represent an unmodified oligonucleotide or an oligonucleotide analog. Thus, oligonucleotides hybridizable to the bcr-abl mRNA target sequence finding utility in the present invention include not only oligomers of the biologically significant native nucleotides, i.e., A, dA, G, dG, C, dC, T and U, but also oligonucleotide species which have been modified for improved stability and/or lipid solubility. For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Nonionic oligonucleotides such as these are characterized by increased resistance to nuclease hydrolysis and/or increased cellular uptake, while retaining the ability to form stable complexes with complementary nucleic acid sequences. The alkylphosphonates in particular, are stable to nuclease cleavage and soluble in lipid. The preparation of alkylphosphonate oligonucleosides is disclosed in U.S. Pat. No. 4,469,863. The methylphosphonates, in particular, are preferred.

Methylphosphonate oligomers can be prepared by a variety of methods, both in solution and on insoluble polymer supports (Agrawal and Riftina, *Nucl. Acids Res.,* 6, 3009–3024 (1979); Miller et al., *Biochemistry,* 18, 5134–5142 (1979), Miller et al., *J. Biol. Chem.,* 255, 9659–9665 (1980); Miller et al., *Nucl. Acids Res.,* 11, 5189–5204 (1983), Miller et al., *Nucl. Acids Res.,* 11, 6225–6242 (1983), Miller et al., *Biochemistry,* 25, 5092–5097 (1986); Engels and Jager, *Angew. Chem. Suppl.* 912 (1982); Sinha et al., *Tetrahedron Lett.* 24, 877–880 (1983); Dorman et al, *Tetrahedron,* 40, 95–102 (1984); Jager and Engels, *Tetrahedron Lett.,* 25, 1437–1440 (1984); Noble et al., *Nucl. Acids Res.,* 12, 3387–3404 (1984); Callahan et al., *Proc. Natl. Acad. Sci. U.S.A.,* 83, 1617–1621 (1986); Koziolkiewicz et al., *Chemica Scripta,* 26, 251–260 (1986); Agrawal and Goodchild, *Tetrahedron Lett.,* 38, 3539–3542 (1987); Lesnikowski et al., *Tetrahedron Lett.,* 28, 5535–5538 (1987); Sarin et al., *Proc. Natl. Acad. Sci. U.S.A.,* 85, 7448–7451 (1988)).

The most efficient procedure for preparation of methylphosphonate oligonucleosides involves use of 5'-O-dimethoxytrityldeoxynucleoside-3'-O-diisopropylmethylphosphoramidite intermediates, which are similar to the methoxy or β-cyanoethyl phosphoramidite reagents used to prepare oligodeoxyribonucleotides. The methylphosphonate oligomers can be prepared on controlled pore glass polymer supports using an automated DNA synthesizer (Sarin et al., *Proc. Natl. Acad. Sci. U.S.A.,* 85, 7448–7451 (1988)).

Suitable nucleotide analogs for preparation of the antisense oligonucleotides described herein include but are not limited to the ethyl or methyl phosphorate analogs disclosed by U.S. Pat. No. 4,469,863 and the phosphorothioate modified oligodeoxynucleotide described by LaPlanche, et al., *Nucleic Acids Research* 14, 9081 (1986) and by Stec et al., *J. Am. Chem. Soc.* 106, 6077 (1984). The general synthetic method for phosphorothioate oligonucleotides was modified by Stein et al., *Nucl. Acids Res.* 16, 3209–3221 (1988), so that these compounds may readily be synthesized on an automatic synthesizer using the phosphoramidite approach.

Resistance to nuclease digestion may also be achieved by modifying the internucleotide linkage at both the 5' and 3' termini with phosphoroamidites according to the procedure of Dagle et al., *Nucl. Acids Res.* 18, 4751–4757 (1990).

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., *Proc. Natl. Acad. Sci. U.S.A.* 86, 3474–3478 (1989)).

Phosphorothioate oligodeoxynucleotides are described by LaPlanche, et al., *Nucleic Acids Research* 14, 9081 (1986) and by Stec et al., *J. Am. Chem. Soc.* 106, 6077 (1984). The general synthetic method for phosphorothioate oligonucleotides was modified by Stein et al., *Nucl. Acids Res.,* 16, 3209–3221 (1988), so that these compounds may readily be synthesized on an automatic synthesizer using the phosphoramidite approach.

Furthermore, recent advances in the production of oligoribonucleotide analogues mean that other agents may also be used for the purposes described here, e.g., 2'-O-methylribonucleotides (Inove et al., *Nucleic Acids Res.* 15, 6131 (1987)) and chimeric oligonucleotides that are composite RNA-DNA analogues (Inove et al., *FEBS Lett.* 215, 327 (1987)).

While inhibition of bcr-abl mRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides are preferred in the practice of the present invention. Oligodeoxyribonucleotides are further preferred because, upon hybridization with bcr-abl mRNA, the resulting DNA-RNA hybrid duplex is a substrate for RNase H, which specifically attacks the RNA portion of DNA-RNA hybrid. Degradation of the mRNA strand of the duplex releases the antisense oligodeoxynucleotide strand for hybridization with additional bcr-abl messages.

The bcr-abl antisense oligonucleotides may be administered to the patient in the form of an appropriate pharmaceutical composition. Alternatively, the antisense oligonucleotides may be administered ex vivo, to cells harvested from the patient. Thus, according to a preferred embodiment of the invention, the bcr-abl antisense oligonucleotides are utilized as bone marrow purging agents for in vitro cleansing of the patient's bone marrow contaminated by $Ph^1$-positive leukemic cells. The antisense oligonucleotides are believed useful as purging agents in either allogeneic or autologous bone marrow transplantation.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188, incorporated herein by reference. Sufficient marrow is withdrawn so that the recipient, who is either the donor (autologous transplant) or another individual (allogeneic transplant), may receive from about $4 \times 10^8$ to about $8 \times 10^8$ processed marrow cells per kg of body weight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with antisense oligonucleotides in a suitable carrier, advantageously in a concentration of about 8 mg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881, incorporated herein by reference.

Other methods of preparing bone marrow for treatment with antisense oligonucleotide may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the bcr-abl antisense oligonucleotides. Such hematopoietic growth factors include, for example, IL-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused back into the patient. For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo use, the bcr-abl antisense oligonucleotides are preferably administered parenterally, most preferably intravenously. The vehicle is designed accordingly. It is also possible to administer such compounds ex vivo by isolating white cells from peripheral blood, treating them with the antisense oligonucleotides, then returning the treated cells to the peripheral blood of the donor. Ex vivo techniques have been utilized in treatment of cancer patients with interleukin-2 activated lymphocytes, and are well-known to those skilled in the art.

In addition to administration with conventional carriers, the antisense oligonucleotides may be administered by a variety of specialized oligonucleotide delivery techniques. For example, oligonucleotides may be encapsulated in liposomes for therapeutic delivery. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature. Oligonucleotides have been successfully encapsulated in unilameller liposomes.

Reconstituted Sendai virus envelopes have been successfully used to deliver RNA and DNA to cells. Arad et al., *Biochem. Biophy. Acta.* 859, 88–94 (1986).

Antisense oligomers have also been delivered in the form of poly(L-lysine) conjugates. Such conjugates are described by Lemaitre et al., *Proc. Natl. Acad. Sci. U.S.A.*, 84, 648–652 (1987).

For ex vivo antineoplastic application, such as, for example, in bone marrow purging, the bcr-abl antisense oligonucleotides may be administered in amounts effective to kill $Ph^1$-positive cells while maintaining the viability of normal hematologic cells. Such amounts may vary depending on the extent of the particular patient's neoplasm, the particular oligonucleotide utilized, the relative sensitivity of the neoplasm to the oligonucleotide, and other factors. Concentrations from about 10 to 200 µg/ml per $10^5$ cells may be employed, preferably from about 40 to 150 µg/ml per $10^5$ cells. Supplemental dosing of the same or lesser amounts of oligonucleotide are advantageous to optimize the treatment. Thus, for purging bone marrow containing $2 \times 10^7$ cell per ml of marrow volume, dosages of from about 2 to 40 mg antisense per ml of marrow may be effectively utilized, preferably from about 8 to 24 mg/ml. Greater or lesser amounts of oligonucleotide may be employed.

For in vivo use, the bcr-abl antisense oligonucleotides may be administered in an amount sufficient to result in extracellular concentrations approximating the above-stated in vitro concentrations. Such amounts may vary depending on the extent of the neoplasm, the particular oligonucleotide utilized, and other factors. The actual dosage administered may take into account the size and weight of the patient, whether the nature of the treatment is prophylactic or therapeutic in nature, the age, health and sex of the patient, the route of administration, and other factors. Those skilled in the art should be readily able to derive suitable dosages and schedules of administration to suit the specific circumstance. The daily dosage may range from about 0.1 to 1,000 mg oligonucleotide per day, preferably from about 10 to about 1,000 mg per day. Greater or lesser amounts of oligonucleotide may be administered, as required.

Based upon the in vivo study described herein, it is believed that a course of treatment may advantageously comprise infusion of the recommended daily dose of oligonucleotide for a period of from about 6 to about 28 days, more preferably from about 9 to about 12 days. Those skilled in the art should readily be able to determine the optimal dosage in each case.

For an adult human being, a daily dose of about 50 mg oligonucleotide per kg of body weight is believed sufficient to achieve an effective extracellular concentration of 1–10 µM.

The invention presents a strategy for treatment of leukemia which is based on the specific inhibition of the expression of genes that confer a growth advantage to neoplastic cells. Thus, the invention provides the opportunity to selectively eliminate those cells. By contrast, most cancer treatments are based on either blocking enzymatic pathways or randomly interacting with DNA irrespective of cell phenotype. Accordingly, any preferential killing of neoplastic cells over normal cells by a particular drug exploits differences in metabolic processes (e.g., growth rate) between normal and cancer cells rather than specific effects of that drug on genetically defined characteristics of the neoplastic cells.

The present invention is described in greater detail in the following non-limiting examples. Examples 1 through 6 comprise in vitro studies, revealing the simultaneous suppression of $Ph^1$ leukemic cell proliferation and a sparing of the growth of normal marrow progenitors, by synthetic oligodeoxynucleotides complementary to the breakpoint junction. These experiments demonstrate the feasibility of gene-targeted selective killing of neoplastic cells.

In Examples 7–12, an in vivo model of leukemic growth (Kamel-Reid et al, Science 246, 1597 (1989); Cesano et al., Blood 77, 2463 (1991); Dick, Cancer Cells 3, 39 (1991)) is employed to show that bcr-abl antisense oligodeoxynucleotides effectively suppress leukemia cell growth in vivo. Severe combined immunodeficient (SCID) mice injected with leukemia cells developed a disease process closely resembling that in humans. Mice treated with bcr-abl antisense were protected from the disease. The cell-associated accumulation of antisense oligomer in various organs reached 4–60 µM, which is more than adequate to inhibit growth of leukemic cells. (See FIG. 7). Extracellular concentrations of phosphorothioate oligodeoxynucleotide in this range were not toxic in vitro for colony forming cells derived from bone marrow of healthy human donors, but very efficiently inhibited growth of primary leukemic cells from CML blast crisis patients (data not shown).

EXAMPLE 1

Effect of bcr-abl Antisense Oligonucleotides on Patient Cells Expressing b2a2 Junction A. Cell harvesting Leukemia cells were obtained from the marrow of the posterior iliac crest of five CML patients in blast crisis. The cells were diluted 1:2 in Iscove's modified Dulbecco medium (IMDM) to form a cell suspension. Philadelphia chromosome-positive blast cells were isolated by Ficoll-Hypaque density gradient sedimentation to remove non-mononuclear cells. Accordingly, the bone marrow cell suspension was gently overlayed on a Histopaque density gradient (Sigma Chemical Co., St. Louis, Mo.) in a 2:1 ratio, and then spun down for 30 min. at 1500 rpm and 18° C. Cells remaining in the interface layer after centrifugation were collected using a Pasteur pipet, and washed with IMDM at 1000 rpm and 40° C. for 10 min.

B. Breakpoint sequencing

Cells plated into methyl cellulose semisolid media after 7–11 days of culture were recovered from the medium. Total RNA was isolated according to the procedure of Chomczynski et al, Anal. Biochem. 162, 156–159 (1987). The RNA (6.1–5 µg) isolated from one patient having particularly exuberant cell growth was annealed with the 3' RT-PCR primer GCTTCACACC ATTCCCCATTGT (SEQ ID NO:10) complementary to 22 nucleotides of c-abl exon 2 for 30 minutes at 37° C. Following annealing of the 3' primer, the RNA was reverse transcribed with 500 units of Moloney murine leukemia virus reverse transcriptase at 37° C. for 1 hour. The reaction was stopped and the mixture diluted in 1 x Thermus aquaticus (Taq) polymerase buffer. A 5' primer, the 22 nucleotide oligomer CACAGCATTC CGCTGAC-CAT CA (SEQ ID NO: 11) complementary to bcr exon 2 and additional c-abl exon 2 3' primer were added to a final concentration of 2 ng/µl each with 2.5 units of Taq polymerase for amplification of the cDNA fragments. Sixty cycles of PCR were performed in a Perkin Elmer Thermal Cycler by annealing at 55° C., synthesizing at 72° C. and denaturing at 95° C. The amplification product, corresponding to the b2a2 junction, was thereafter separated on a 2% agarose gel. The band containing the bcr-abl fragment was cut out and cleaned according to a standard technique utilizing a GENE-CLEAN™ kit (Bio 101, Inc.), cloned by blunt end ligation in the BLUESCRIPT SK vector (Stratagene Cloning Systems) linearized by SMA I digestion. Several individual clones were then sequenced using the SEQUENASE™ version 2.0 enzyme (United States Biochemical Corp., Cleveland, Ohio), according to the sequence protocol recommended by the manufacturer. Accordingly, the denatured bcr-abl DNA fragments were annealed with specific primers which flank the cloning site in the BLUESCRIPT SK vector, in the presence of SEQUENASE™ reaction buffer for 15 min. at 37° C. The primer-annealed fragments were incubated at room temperature with SEQUENASE™ version 2.0 enzyme and $\alpha$-$S^{35}$dAT at 37° C. Subsequently, labelled template-primer complexes were transferred to tubes containing A, T, C and G nucleotides (one nucleotide per tube) and incubated 5–30 min. at 37° C. The samples were then loaded on a previously prepared acrylamide gel, and run for approximately 10 hours. The sequencing gel was dried, and the film exposed O/N. Sequence analysis of several of the individual clones identified the bcr-abl junction as having the cDNA sequence shown in FIG. 1 (SEQ ID NO:1). The arrow in the figure indicates the bcr-abl breakpoint junction, and the box delineates the 18 nucleotides corresponding to the junction, which forms a preferred target sequence for hybridization of antisense oligomer. The junction corresponds precisely to the L-6 type breakpoint reported by Shtivelman et al., Cell 47, 277 (1986), in which the bcr exon 2 is fused to c-abl exon 2.

In a similar manner, L-6 type junctions were identified in the remaining CML blast crisis patients by hybridization of RT-PCR amplification products derived from blast crisis CML RNA using a synthetic 18-mer GAAGGGCTTC TTC-CTTAT (SEQ ID NO:3) specific for the 18-nucleotide target sequence of the L-6 bcr-abl junction. This "antisense" oligomer, complementary to nine nucleotides corresponding to bcr, and 9 nucleotides corresponding to c-abl, was synthesized using a model 380 B DNA synthesizer (Applied Biosystems, Inc., Foster City, Calif.). Sequence analysis of the cloned breakpoint demonstrated that in each of the four cases, the junction was identical to that shown in FIG. 1.

C. Oligomer treatment.

Figure 2B:
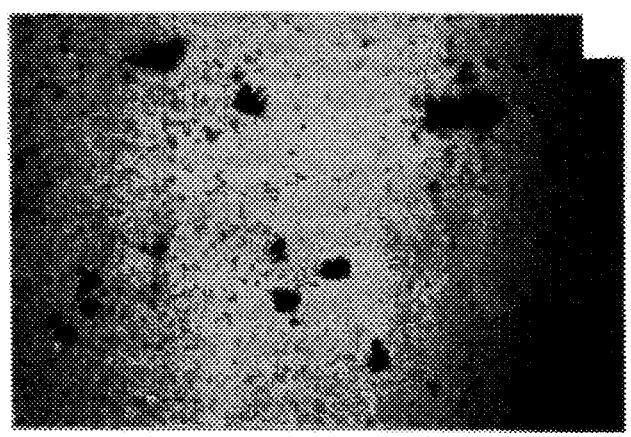
Figure 2C:
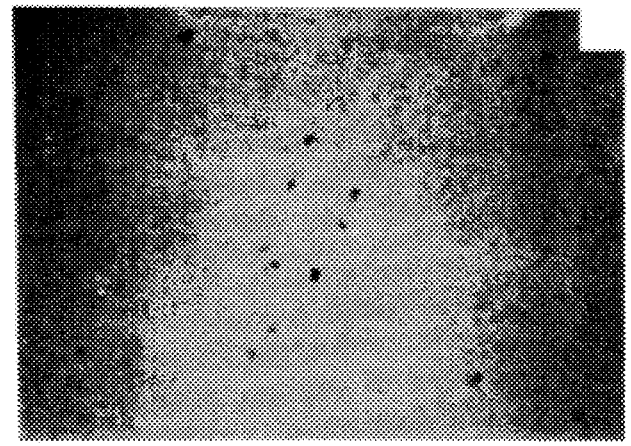

Blast cells (0.5×10⁵ cells) were placed in 0.4 ml of liquid suspension cultures (Iscove's modified Dulbecco's medium with 2% human B serum) in the presence of interleukin-3 (IL-3, 20 u/ml) and granulocyte macrophage colony stimulating factor (GM-CSF, 5 ng/ml) to stimulate cell colony formation. In addition to the GAAGGGCTTC TTCCTTAT (SEQ ID NO:3) oligomer, which is completely complementary to the target sequence, the mismatched (4 nucleotide substitutions) bcr-abl antisense oligomer GAACGGCATC TACGTTAT was also prepared (SEQ ID NO:2). The IL-3/GM-CSF treated cultures received 40 µg/ml (1 µg/ml =0.35 µM) of oligonucleotide at the start of the culture period and 20 µg/ml 18 hours later. Control cultures were left untreated. Four hours after the second addition of oligonucleotides to the cultures, cells were directly seeded into duplicate methylcellulose dishes containing IL-3 (20 U/ml) and GM-CSF (5 ng/ml). Cells placed into semi-solid cultures were allowed to grow for an additional 10 days. The plates were then scanned with an inverted microscope and total numbers of colonies and clusters were counted. $Ph^1$-positive blast cells were, in some cases, cultured in absence of hematopoietic growth factors; in these conditions the colonies were fewer and smaller than in the presence of growth factors. Untreated cells and cells exposed to the mismatched oligomer formed numerous colonies of blast cells (FIG. 2A and 2B, respectively), whereas very few colonies, with a much smaller number of cells, formed in the presence of bcr-abl antisense oligonucleotide (FIG. 2C). Inhibition of colony formation derived from blast cells from the five L-6 type junction patients ranged from 60 to 90% in repeated experiments. See Table 1. In contrast, the number of colonies formed from normal progenitors was essentially identical in the presence or absence of synthetic oligomers (not shown).

TABLE 1

| | Number of Colonies | | |
|---|---|---|---|
| Patient | Untreated | Antisense-treated | % Inhibition |
| 1 | 450 ± 64 | 112 ± 18 | 75 |
| 2 | 324 ± 18 | 62 ± 8 | 82 |
| 3 | 480 ± 88 | 50 ± 12 | 90 |
| 4 | 212 ± 15 | 80 ± 8 | 60 |
| 5 | 380 ± 16 | 70 ± 8 | 82 |

EXAMPLE 2

Effect of bcr-abl Antisense Oligonucleotide on Patient Cells Expressing b3a2 Junction A. Breakpoint sequencing.

To identify CML blast crisis patients carrying the second common type junction, in which bcr exon 3 is juxtaposed to c-abl exon 2, total RNA derived from cells of CML patients in blast crisis was reverse-transcribed with synthetic primers. The 3' primer (SEQ ID NO:10) was complementary to 22 nucleotides of c-abl. exon 2. The 5' primer was the 22-mer GTCATCGTCC ACTCAGCCAC TG (SEQ ID NO:12) complementary to 22 nucleotides of bcr exon 3. The RNA was amplified by polymerase chain reaction according to Example 1. The amplification products were then hybridized with the synthetic 18-mer oligonucleotide GAAGGGCTTT TGAACTCT (SEQ ID NO:6), which is complementary to the b3a2 junction. After cloning of breakpoints in two patients, sequence analysis of several clones identified the b3a2 junction as precisely corresponding to the K-28 breakpoint shown in FIG. 3. (SEQ ID NO:4).

B. Oligomer treatment.

Figure 4A:
FIGS. 4A, 4B and 4C are similar to FIGS. 2A, 2B and 2C, and comprise 10-day CML cell cultures containing cells from patients in blast crisis expressing the bcr-abl K-28 type junction shown in FIG. 3. Cells were untreated (FIG. 4A); treated in vitro with an 18-mer antisense oligonucleotide (SEQ ID NO:5) complementary to the target sequence of FIG. 3, but containing two nucleotide mismatches (FIG. 4B); or treated with an 18-mer antisense oligonucleotide (SEQ ID NO:6) completely complementary to the same target sequence (FIG. 4C).
Figure 4B:
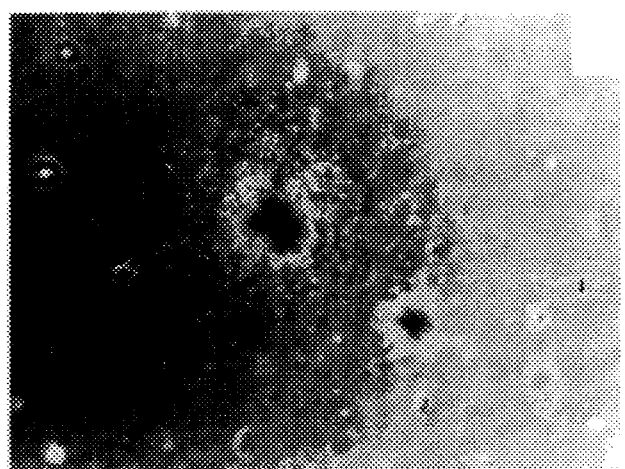
Figure 4C:

Utilizing the culture condition and oligomer treatment conditions of Example 1, cells were exposed to either no oligomer (FIG. 4A), the 18-nucleotide synthetic oligomer GAAGTGCTGT TGAACTCT (SEQ ID NO:5) partially complementary to the b3a2 junction, containing 9 nucleotides corresponding to bcr and 9 nucleotides corresponding to c-abl but with two mismatches (FIG. 4B); or the 18-nucleotide synthetic oligomer GAAGGGCTTT TGAACTCT (SEQ ID NO:6) completely complementary to the same bcr-abl junction (FIG. 4C).

In the above two patient cases with the K-28 breakpoint, the inhibition of colony formation with authentic bcr-abl antisense oligomer (SEQ ID NO:6) ranged, in two duplicate experiments, from 60% to 70%, as set forth in Table 2.

TABLE 2

| | Number of Colonies | | |
|---|---|---|---|
| Patient | Untreated | Antisense-treated | % Inhibition |
| 1 | 278 ± 28 | 102 ± 14 | 65 |
| 2 | 182 ± 18 | 68 ± 12 | 63 |

Cells from the same patients carrying the K-28 type breakpoint were also exposed to the antisense oligomer (SEQ ID NO:3) complementary to the L-6 type junction. No significant reduction of colony formation (2.5–5% inhibition) was observed with this oligomer in comparison to untreated cells, further demonstrating the specificity of the observed effect for cells treated with the 18-mer antisense oligonucleotide (SEQ ID NO:6) completely complementary to the K-28 junction (FIG. 4C).

EXAMPLE 3

Effect of bcr-abl Oligomer Exposure on Normal Hematopoietic Progenitor Cell Growth.

The following experiment demonstrates the specificity of bcr-abl antisense oligonucleotides for leukemic cells, leaving normal hematopoietic progenitor cells completely unaffected.

Normal bone marrow mononuclear cells (MNC) were obtained by aspiration from consenting volunteers and enriched for hematopoietic progenitors as previously reported by numerous investigators (Zamecnick et al., Proc. Natl. Acad. Sci. U.S.A. 83, 4143–4147 (1986); Caracciolo et al., J. Clin. Invest. 85, 55–61 (1990)). In brief, marrow cells were subjected to Ficoll-Hypaque density gradient sedimentation and then depleted of adherent monocyte-macrophage and T-lymphocytes by adherence to plastic Petri dishes and rosetting with neuraminidase-treated sheep red blood cells, respectively. Philadelphia chromosome-positive blast cells were isolated by Ficoll-Hypaque density gradient sedimentation from a CML patient in blast crisis (L-6 type junction). Morphological analysis revealed that >95% of the cells were blast. The residual non-blast cells had the morphological appearance of small lymphocytes. 25,000 MNC and 25,000 CML blast cells were combined and incubated with bcr-abl breakpoint-Specific antisense oligomer (SEQ ID NO:3) (40 µg/ml at h 0; 20 µg/ml 18 hours later) or with a 4 nucleotide mismatch bcr-abl antisense oligomer (SEQ ID NO:2) (40 µg/ml at 0 h; 20 µg/ml 18 hours later) or left untreated. Four hours after the second addition of oligonucleotides to the cultures, cells were seeded into duplicate methylcellulose dishes containing IL-3 (20 U/ml) and GM-CSF (5 ng/ml) and allowed to grow for an additional 12 days. At the end of the incubation period colonies were counted.

After twelve days in culture, it was apparent that the number of colonies arising from the CML blast crisis cells (leukemia-colony forming units, "CFU-L") exposed to the bcr-abl antisense oligomer was much lower than that arising in the presence of the mismatched bcr-abl oligomer. The data is shown in Table 3, below, wherein values represent mean ± standard deviation of duplicate control cultures (no oligonucleotide added) and duplicate experimental cultures from two separate experiments. Colony forming unit-granulocyte macrophage (CFU-GM)-derived colonies consisted of 50 or more cell aggregates, while CFU-GM-derived clusters were defined as aggregates of between 4 and 40 cells. These are normal hematopoietic colonies derived from progenitors with the capability to differentiate along the granulocytic and macrophage lineages. In contrast, the number of colonies formed from normal progenitors was essentially the same in the presence or absence of synthetic oligomers.

TABLE 3

| Oligonucleotide | Colonies or Clusters | | |
| --- | --- | --- | --- |
| | CFU-GM | CFU-L* | CFU-GM + CFU-L** |
| Control (no oligomer added) | 263 ± 10 | 806 ± 70 | 978 ± 24 |
| bcr-abl antisense with 4 nucleotide mismatches | 265 ± 6 | 786 ± 23 | 900 ± 46 |
| bcr-abl antisense with no mismatches | 253 ± 35 | 180 ± 14 | 450 ± 42 |

*CFU-L = colonies formed from CML blast crisis cells.
**CFU-GM ± CFU-L = colonies formed from 1:1 mixtures of normal marrow progenitors and CML blast crisis cells.

The formed colonies were removed from the methylcellulose plates to determine whether residual colonies consisted of normal or leukemic cells. Cells derived from the residual colonies removed from the plates were isolated and morphologically identified by Giemsa staining. Only blast cells were identified in colonies arising from CML blast crisis cells. In the 1:1 mix of normal MNC and CML blast crisis cells exposed to mismatched (4 nucleotide substitutions) bcr-abl oligomer, the isolated cells were, as expected, heterogeneous and consisted of blast cells and a variety of differentiating elements. In the 1:1 mix of normal MNC and CML blast crisis cells exposed to authentic bcr-abl antisense oligomer (no mismatches), the isolated cells largely consisted of differentiating elements, thus suggesting the persistence of normal progenitors and the selective depletion of leukemic blast cells.

EXAMPLE 4

Analysis of bcr-abl Expression of Residual Cells

To provide unambiguous evidence of the elimination of Philadelphia chromosome blast cells, residual cells from Example 3 were evaluated for the expression of bcr-abl transcripts, since the levels of this transcript should reflect the number of surviving leukemia cells. For this purpose, total RNA was isolated from a pool of colonies from Example 3, and the levels of bcr-abl transcripts were evaluated. Levels of $\beta_2$-microglobulin transcript were also determined as a control. The $\beta_2$-microglobulin gene is expressed independent of cell cycle.

Accordingly, bcr-abl and $\beta_2$-microglobulin transcripts were reverse-transcribed and amplified in the presence of specific primers and Taq polymerase as described by Rappollee, Science 241, 708–712 (1988). The amplification products were separated on a 2% agarose gel and transferred to a nitrocellulose filter, which was hybridized with a synthetic 40-nucleotide c-abl fragment and a 40-nucleotide $\beta_2$-microglobulin fragment and labeled with [$\gamma$-$^{32}$P]-ATP and polynucleotide kinase. The c-abl probe recognizes the amplified 257-nucleotide sequence of FIG. 1, which contains the L-6 type bcr-abl junction. The $\beta_2$-microglobulin probe recognizes the 195-nucleotide sequence contained within 5' and 3' $\beta_2$-microglobulin primers (Id.; Suggs et al., Proc. Natl. Acad. Sci. U.S.A. 78, 6613 (1981)). No bcr-abl transcript was detected in RNA isolated from the colonies arising from mixed cell populations exposed to bcr-abl antisense oligonucleotide. By contrast, the expression of $\beta_2$-microglobulin, used as a control, was clearly detectable in the antisense-treated colonies, indicating the selective reduction of cells carrying the bcr-abl translocation, and the survival of a progeny arising from normal progenitors.

The data indicate that, in the context of the natural disease, a functional bcr-abl gene is necessary to maintain the abnormal growth associated with the Ph$^1$-positive leukemic phenotype. Since the synthetic oligomers do not affect the growth of normal progenitors, leukemic growth may be selectively inhibited based upon the presence of a tumor-specific genetic alteration involving the maintenance of the leukemic phenotype. Synthetic oligonucleotides complementary to the bcr-abl hybrid gene synthesized on an individual patient basis thus may be used to selectively affect the growth of leukemic cells, once the specific bcr-abl junction is identified.

Proliferation of Ph$^1$-positive ALL cells expressing the b1a2 junction were inhibited with antisense oligonucleotides according to Example 5.

EXAMPLE 5

Effect of bcr-abl Antisense Oligonucleotides on Cell Line Expressing b1a2 Junction A. Breakpoint sequencing.

RNA was isolated from cell line ALL-1 derived from a Ph$^1$-positive ALL patient (Erikson et al. Proc. Natl. Acad. Sci. U.S.A. 83, 1807–1811 (1986)). Cloning and sequencing of the breakpoint junction were carried out as in Example 1 utilizing as the 5' primer, the 22 nucleotide oligomer CAA-CAGTCCT TCGACAGCAG CA (SEQ ID NO:13) complementary to bcr exon 1, and as the 3' primer, the 22 nucleotide oligomer (SEQ ID NO:10) complementary to c-abl exon 2. The 18-mer breakpoint sequence GAGACGCAGA AGC-CCTTC (SEQ ID NO:14) confirmed the published sequence of Fainstein et al., Nature 330, 386–388 (1987).

B. Oligomer treatment.

Figure 6:
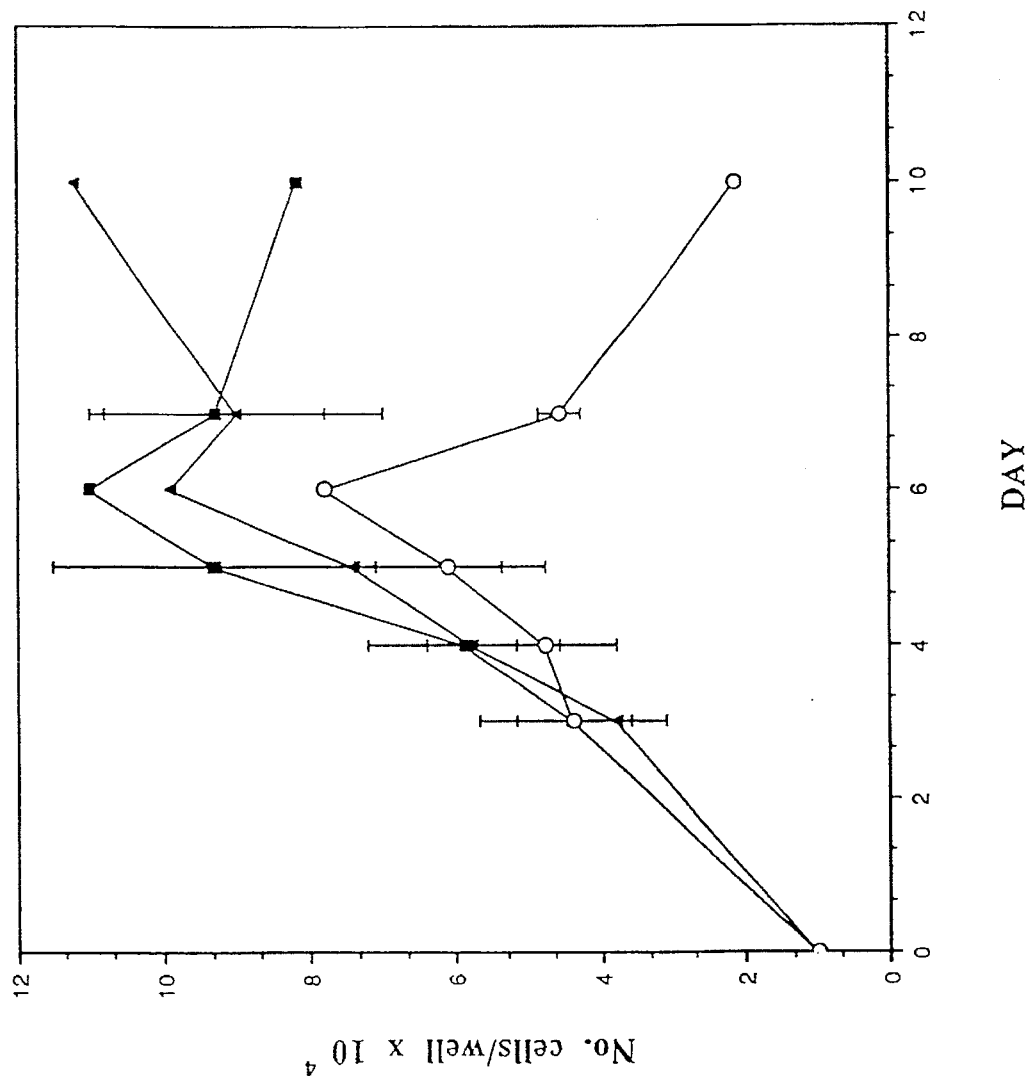
FIG. 6 is a cell number plot of leukemic cells in culture from the same Ph$^1$-positive ALL cell line. Cells were untreated (-■-); treated in vitro with an 18-mer antisense oligonucleotide (SEQ ID NO:8) complementary to the target sequence of FIG. 5, but containing two nucleotide mismatches (-▲-); or treated with an 18-mer antisense oligonucleotide (SEQ ID NO:9) completely complementary to the same target sequence (-○-).

Ph$^1$-positive cells (1–2×10$^4$ cells in 500 μl were cultured (i) in the absence of oligomer, (ii) in the presence of the 18-mer antisense oligonucleotide GCAGGGCTTC TACGTCTC (SEQ ID NO:8) complementary to the b1a2 bcr-abl breakpoint junction, but containing two nucleotide mismatches, or (iii) in the presence of the 18-mer antisense oligonucleotide GAAGGGCTTC TGCGTCTC (SEQ ID NO:9) completely complementary to the same junction. The cultures were exposed to 50 μg of oligomer at time zero, and 25 μg/ml at 24 hours and at 48 hours. Cells were counted daily. The results are shown in FIG. 6 where (-■-) denotes control cultures (no oligomer), (-▲-) denotes cultures to which the 2-mismatch oligomer was added, and (-○-) denotes cultures to which the completely complementary antisense oligomer was added. Cultures treated with antisense oligomer achieved a significant reduction in leukemic cell number over the control and mismatch-treated cultures.

EXAMPLE 6

Effect of Phosphorothioate Antisense Oligonucleotide on Cell Line Expressing b2a2 Junction Karyotypic analysis of the Philadelphia chromosome-positive leukemia cell line BV173 (Pegoraro et al., *J. Natl. Canc. Inst.* 70, 447 (1983)) revealed the 9;22 translocation as the only chromosomal abnormality in each of 20 metaphases analyzed. Amplification of the bcr-abl junction with a 5' primer corresponding to bcr exon 2, and a 3' primer corresponding to abl exon 2, followed by hybridization to an 18-mer specific for the b2/a2 or the b3/a2 junction identified the b2/a2 breakpoint in these cells (data not shown).

The sensitivity of the BV173 cells to b2/a2 antisense phosphorothioate oligodeoxynucleotides was assessed. Phosphorothioate oligodeoxynucleotides were prepared on either an Applied Biosystems Model 380B or 390Z Automated Synthesis instrument using conventional phosphoramidite monomers and manufacturer-recommended procedures, which included substitution of tetraethylthiuran (or an equivalent sulfur-donor reagent) for iodine-water-pyridine, reversing the normal oxidation-then-cap sequence within each cycle, reversed-phase preparative chromatography, detritylation, and obtaining the final product in the form of its sodium salt, all according to previously published methodology: Zon and Stec, in *Oligonucleotides and Analogues A Practical Approach*, F. Eckstein, Ed. (Oxford Univerisity Press, Oxford 1991), pp. 87–108; Zon and Geiser, *Anti-Cancer Drug Design* 6, 539 (1991); Vu and Hirschenbein, *Tetrahedron Lett.* 32, 3005–3008 (1991).

Figure 7:
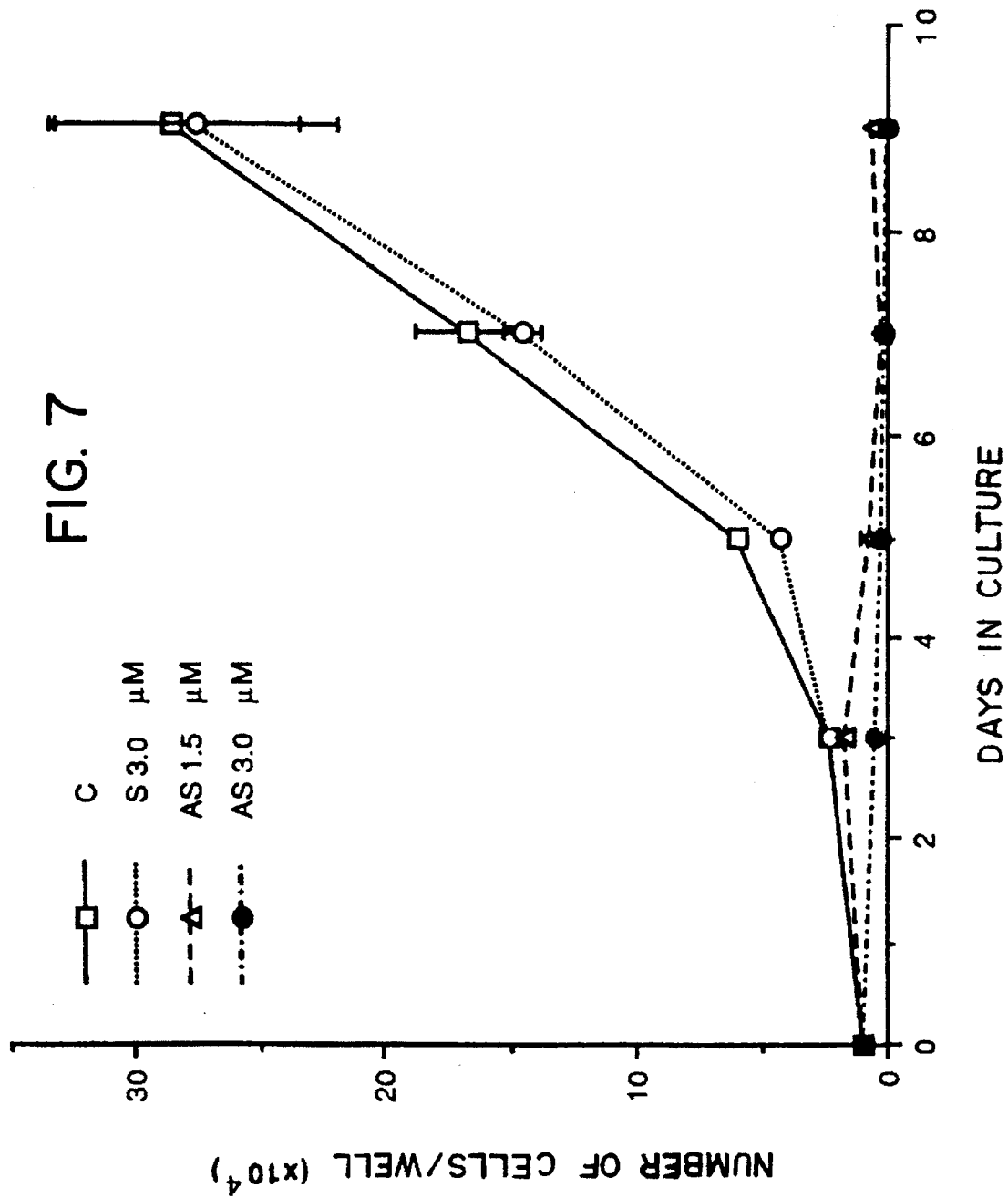
FIG. 7 is a cell number plot of the Ph$^1$-positive leukemic cell line BV173 growing exponentially in culture ($1 \times 10^5$ cells/ml). Cells were untreated (-□-); treated in vitro with a 23-mer b2a2 sense phosphorothioate oligodeoxynucleotide (-○-, SEQ ID NO:34, final concentration 3 μM); or 26-mer b2a2 antisense phosphorothioate oligodeoxynucleotide (-Δ-, SEQ ID NO:29, final concentration; 1.5 μm -●-, 3 μM).

BV173 cells were cultured in the presence of phosphorothioate b2/a2 antisense 26-mer CGCTGAAGGG CTTCT-TCCT ATTGAT (SEQ ID NO:29), the phosphorothioate sense sequence ATCAATAAGG AAGCCCTTCA GCG (SEQUENCE ID NO:34), or the b3/a2 (SEQ ID NO:31) or b1/a2 (SEQ ID N0:33) phosphorothioate antisense 26-mer. Only the b2/a2 antisense oligodeoxynucleotide inhibited the proliferation of BV173 cells (FIG. 7), and in repeated experiments, inhibition was 97.6 and 100% using antisense oligodeoxynucleotides at concentrations of 1.5 µM (FIG. 7, -Δ-) and 3.0 µM (FIG. 7, -●-) respectively, after 9 days in culture. The sense oligomer SEQ ID NO:34 gave no inhibition (FIG. 7, -○-) in comparison to untreated control cells (FIG. 7, -□-).

EXAMPLE 7

In Vivo Protection of Mice From Leukemia by b2a2 Antisense Oligonucleotide

SCID mice injected with BV173 cells were protected from disease by b2a2 phosphorothioate oligodeoxynucleotides, according to the following experiment. Injection of the mice with BV173 cells induces a disease closely resembling that in human leukemia patients.

A. Determination of Lethal BV173 Cell Dose

To determine the lethal dose of BV173 cells in the SCID mice, we injected from $10^3$ to $10^7$ cells into the tail vein and monitored survival at various times postinjection. Mice injected with $10^7$, $10^6$, $10^5$, or $10^4$ BV173 cells died 8–10, 9–12, 13–15, or 14–22 weeks later, respectively, due to leukemia cell growth as confirmed on necroscopy. Spleen weight was about 40 times higher than that in noninjected SCID mice while liver and kidneys had numerous metastases and were enlarged 10-fold as compared to non-injected mice. Mice injected with $10^3$ BV173 cells were still alive 35 weeks post implantation, and leukemia was never detected. From this study, $10^6$ cells was taken as a lethal dose.

B. Assay For Leukemic Disease State

Spreading of the disease process was monitored by three different assays that allow determination of the number of infiltrating human leukemic cells in murine tissues.

A first assay comprised an immunofluorescence analysis of cALL antigen (CALLA)-positive cells. All BV173 cells but not normal murine hematopoietic cells express this antigen (assay sensitivity=$10^{-2}$). Single cell suspensions were prepared for flow cytometry analysis from peripheral blood, spleen and bone marrow cells of the leukemic SCID mice by centrifugation on a lymphocyte-M gradient (Cedarlane Labs, Ltd., Ontario, Canada). Cells ($1 \times 10^5$) were stained with the FITC-conjugated mouse anti-CALLA monoclonal antibody (Becton-Dickinson Immunocytometry Systems, San Jose, Calif.) to human CD10 antigen. After staining, cells were washed and analyzed by flow cytometry using the Epics Profile Analyzer (Coulter Electronic). For each type of cells two negative controls were used: cells from the same organ of healthy SCID mice stained with FITC-conjugated anti-CALLA, and cell suspensions from leukemic SCID mice stained with anti-human CD3 monoclonal antibody which does not react with BV173 or murine cells.

A second assay for leukemic disease comprised a clonogenic assay in semisolid medium. BV173 cells form colonies in the absence of human growth factors, with a cloning efficiency of 25 to 35%, whereas murine cells do not form colonies (assay sensitivity=$10^3$). Data from 12 plates of 5 healthy SCID mice revealed that only a few colonies from murine cells grew up to 7–9 days after plating, and then began to die; after 12 days in culture there were no colonies of viable cells. By contrast, BV173 cells formed numerous, rapidly growing colonies. To rule out the possibility that the presence of BV173 cells permitted the growth of murine progenitors, mixing experiments were carried out. RT-PCR analysis for detection of bcr-abl (b2/a2) transcripts in individual viable colonies arisen from the mixture of normal murine cells and BV173 cells (after 12 days of culture) indicated that 100% of these colonies (10 colonies analyzed) were leukemic as indicated by the expression the bcr-abl (b2/a2) transcripts (data not shown).

According to a third assay, the extent of leukemic disease was assessed by chain RT-PCR to monitor the expression of b2/a2 transcripts (assay sensitivity=$10^4$) in total RNA isolated from bone marrow cells, splenocytes, peripheral blood leukocytes, liver, lung and brain tissues. Depending on the number of BV173 cells injected, various numbers of leukemic cells were detected by clonogenic assay and RT-PCR in murine tissues, 3 and 6 weeks after injection. A few days before the expected death of leukemic SCID mice, approximately 80, 65, and 10% cALLA-positive cells were detected in bone marrow cells, splenocytes and peripheral blood leukocytes, respectively. RT-PCR revealed BV173 cells in lungs and brain.

C. b2a2 Antisense Treatment

To determine whether synthetic phosphorothioate oligodeoxynucleotides targeted against the bcr-abl junction of BV172 cells would modify the disease process in SCID mice. SCID mice were injected with $10^6$ BV173 cells. The mice then received 1 mg of sense (ATCAATAAGG AAGCCCTTCAGCG, SEQ ID NO:34) or antisense (CGCTGAAGGGCTTCTTCCTT ATTGAT, SEQ ID NO:29) b2/a2 bcr-abl phosphorothioate oligodeoxynucleotides (pyrogen leven <1 Eu/mg; 0.2 ml in Iscove modified Dulbecco medium in 5–10 seconds) intravenously for each of 9 consecutive days, beginning either 7 or 21 days after introducing $10^6$ BV173 cells. Control mice received the diluent (iscove's modified Dulbecco medium) only. These time points approximate distinct disease stages in humans.

D. Results of Antisense Treatment

At 7 (+7) and 21 (+21) days after injecting SCID mice with $10^6$ BV173 cells, single cell suspensions were prepared from various tissues. After lysing red cells with 0.83% $NH_4Cl$ buffered with 0.17 mM Tris-HCl, pH 7.4, total RNA was extracted as described (Chomczynski and Sacchi, *Anal. Biochem.* 162, 156 (1987)) and the suspension was divided into two equal aliquots. Bcr-abl and β-actin transcripts were reverse-transcribed and amplified with specific primers and Taq polymerase as described by Szczylik et al., *Science* 253, 562 (1991). Amplification products were separated on a 2% agarose gel, transferred to a nitrocellulose filter and hybridized with a synthetic 40-base c-abl fragment or 20-base β-actin fragment end-labeled with $[\gamma^{32}\text{-P}]$-ATP and polynucleotide kinase. The c-abl probe recognizes an amplified 257-bp sequence containing the bcr-abl junction: the β-actin probe recognizes a 209-bp fragment, contained within the 5' and 3' β-actin primers (Tokunaga et al., *Nucleic Acids Res.* 14, 2829 (1986)).

Figure 9:
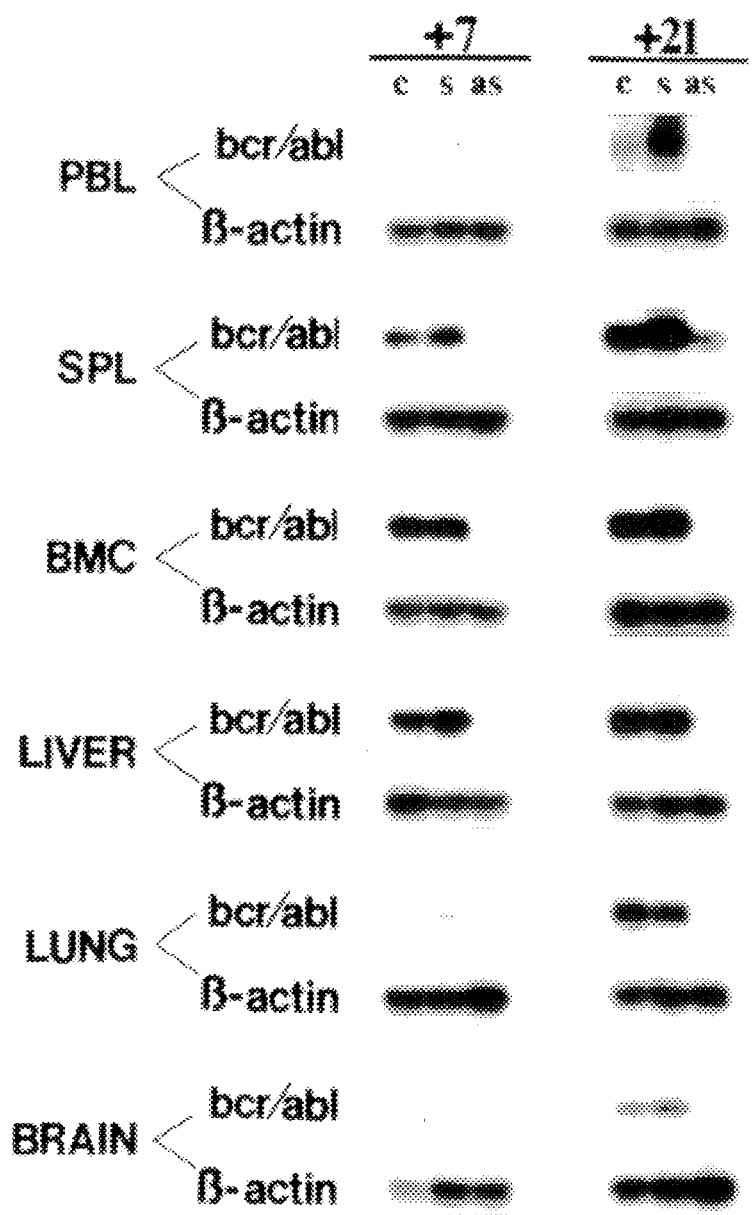
FIG. 9 is similar to FIG. 8, showing the presence or absence of bcr-abl b2a2 and β-actin mRNA transcripts in tissues of mice (PBL=peripheral blood leukocytes; SPL= spleen; BMC=bone marrow cells). Mice also received 1 mg of b2a2 sense ("s", SEQUENCE ID NO:34) or antisense ("as", SEQ ID NO:29) phosphorothioate oligodeoxynucleotide intravenously for each of nine consecutive days beginning either seven (+7) or twenty-one (+21) days after injection with $10^6$ BV173 cells; control mice ("c") received diluent only.

Clonogenic assays from bone marrow cell suspensions of untreated and bcr-abl oligodeoxynucleotides-treated leukemic SCID mice were carried out as follows. $10^5$ cells were plated in duplicate in 35×10 mm tissue culture dishes (Nunc, Inc., Naperville, Ill.) in HCC-4230 medium (Terry Fox Lab., Vancouver, Canada) supplemented with 2.5 mM L-glutamine, and allowed to grow for 12 days. Plates were scanned with an inverted microscope and total colony number was determined. The results are shown in FIG. 9 (C, untreated mouse; S, sense-treated mouse, AS, antisense-treated mouse).

The clonogenic assays indicated only a few colonies (6.0±4.2) derived from bone marrow cell suspensions and immunofluorescence studies were negative for the presence of leukemia. At 21 days after injecting $10^6$ BV173 cells, RT-PCR indicated the presence of leukemic cells in bone marrow, spleen, peripheral blood, liver and lungs, but not in brain (FIG. 8, lane ±21); a very high leukemic colony number 353.0±52.3) was generated from bone marrow and few (4.0±1.4) from spleen. At least 6.0±1.4% of marrow cells were cALLA-positive. Thus, treatment of SCID mice 7 days after injection of leukemic cells would approximate the clinical situation of "minimal residual disease" in humans, whereas such treatment 21 days after injection of $10^6$ leukemic cells mimics the "full blown disease".

Figures 10A, 10B, 10C:
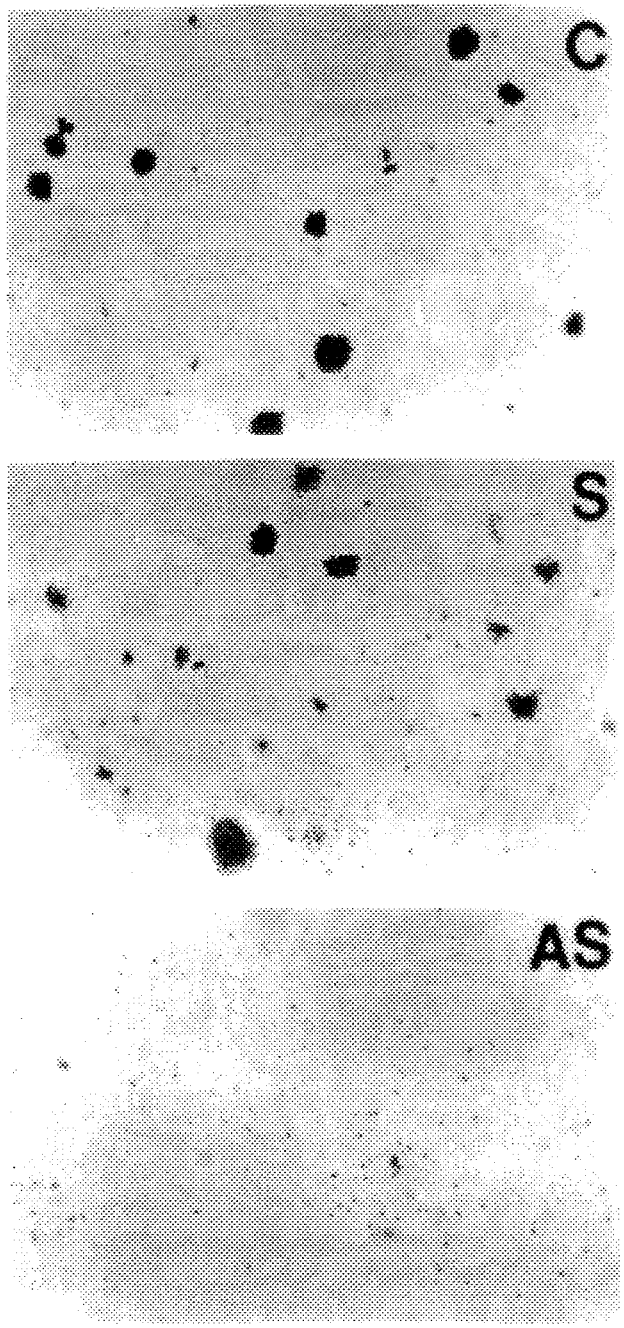
FIG. 10A–10C represent the results of clonogenic assays from bone marrow cell suspensions of the same untreated (FIG. 10A), sense-treated (FIG. 10B, SEQ ID NO:34) and antisense-treated (FIG. 10C, SEQ ID NO:29) mice. Cells ($10^5$) were plated and grown for 12 days and then scanned with an inverted microscope.

RT-PCR analysis of total RNA isolated from peripheral blood, spleen, bone marrow, liver, lung and brain of mice treated for 9 days with phosphorothioate oligodeoxynucleotides beginning 7 days after injection of $10^6$ BV173 cells and killed 12 days after the last treatment (4 weeks of leukemia growth) revealed bcr-abl transcripts in each of the tissues analyzed except brain, in the untreated and sense-treated but not in the antisense-treated mouse (not shown). Clonogenic assays of bone marrow cell suspensions indicated leukemic colonies in high numbers from the untreated and sense-treated mice (353±52 and 380±25, respectively) but not after injection of bcr-abl antisense oligodeoxynucleotides in perfect agreement with the RT-PCR data. CALLA+ cells were detected in bone marrow of control and sense-treated animal. In mice killed 26 days after the last treatment (6 weeks of leukemia growth) with bcr-abl phosphorothioate oligodeoxynucleotides, macroscopic examination revealed, in addition to spleen enlargement, the presence of distinct leukemic nodules in liver and kidneys of the untreated and sense-treated mice, but not in those of the antisense-treated mouse (not shown). RT-PCR analysis of total RNA isolated from peripheral blood leukocytes, spleen, bone marrow, liver, lung and brain revealed no bcr-abl (b2/a2) transcripts in the tissues of the antisense-treated mouse, whereas these were readily detected in each tissue from the untreated and sense-treated mice. (FIG. 9, lanes +7). Likewise, clonogenic assays of bone marrow and spleen cell suspensions demonstrated the presence of numerous leukemic colonies in the untreated (FIG. 9) and sense-treated (FIG. 10B) samples, but not in samples from the bcr-abl antisense-treated mouse (FIG. 10C). A few colonies derived from peripheral blood leukocytes of the sense-treated mouse, but no detectable colonies were generated from the antisense-treated mouse sample. No CALLA+ cells were detected in the tissues of the antisense-treated mouse, whereas such cells were readily detected in bone marrow (16.8±1.8%), spleen (4.1±0.2%) and peripheral blood (1.9±0.2%) of the sense-treated mouse.

Figure 11A:
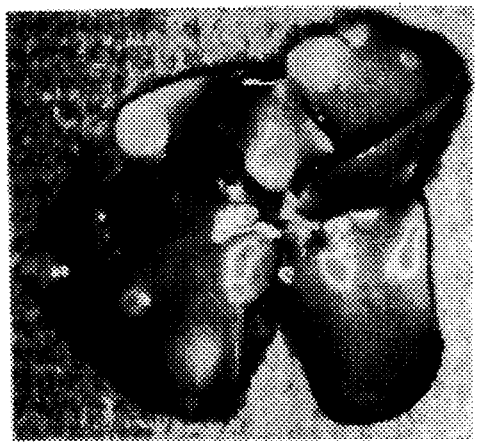
FIGS. 11A and 11B are photographs of livers of the same sense-treated and antisense-treated mice. Numerous distinct leukemic nodules are visible in the liver from the sense-treated mouse (FIG. 11A) but not from the antisense-treated mouse (FIG. 11B).
Figure 11B:

In the mice treated with bcr-abl phosphorothioate oligodeoxynucleotides (1 mg/mouse/day for nine consecutive days) beginning 21 days after injection of $10^6$ BV173 cells and analyzed 12 days after the last treatment (6 weeks after the leukemia implantation) splenomegaly and leukemic metastases in the liver were detected in control and sense-treated mice, but not in antisense-treated mouse. Bcr-abl transcripts were detected in total RNA from peripheral blood mononuclear cells, splenocytes, bone marrow cells, liver, lungs, and brain in the untreated and sense-treated, but not in the antisense-treated mice (not shown). Clonogenic assay from bone marrow cell suspensions revealed a high number of leukemic colonies in the untreated (575.5±83.8) and sense-treated (668.5±59.1) mouse, but not after injection of bcr-abl antisense oligodeoxynucleotides. Likewise, clonogenic assays of spleen and peripheral blood mononuclear cell suspensions demonstrated 80.5±12.0 and 11.0±8.5 colonies in the untreated mouse, 116.0±29.7 and 14.5±4.9 in the sense-treated mouse, and 0 in the antisense-treated mouse (not shown), respectively. Flow cytometry analysis of control and sense treated animals revealed CALLA+ cells in bone marrow (17.7±1.8 and 10.0±0.5%, respectively), spleen (1.9±0.1 and 1.9±0.8%, respectively) and peripheral blood (1.0±0.1 and 0.9±0.1, respectively). CALLA+ cells, however, were not detected after antisense treatment. Macroscopic examination of the mice 26 days after the treatment was completed (8 weeks of leukemia growth) revealed numerous metastases in the liver (FIG. 11A), a few in the kidneys, and splenomegaly in sense-treated mouse, but not in antisense-treated animal (FIG. 11B). Bcr-abl transcripts were undetectable after antisense-treatment in each tissue analyzed except spleen from which an RT-PCR product (less abundant than in the sense-treated mouse) was amplified; in contrast, bcr-abl transcripts were readily detectable in the untreated and sense-treated mice (FIG. 9, lanes +21. Clonogenic assays were in agreement with RT-PCR data, as we detected leukemic colonies in bone marrow (839.5±41.7), spleen (548.5±128.0), and peripheral blood (51.0±41.7), spleen (548.5±128.0), and peripheral blood (51.0±14.1) of sense-treated mouse, but not after antisense treatment. CALLA+ cells were easily detectable after sense-treatment in bone marrow (23.9±5.0%), spleen (9.9±1.8%) and peripheral blood (2.0±0.3%). In contrast, these cells were not detected in the antisense-treated mouse.

C. Summary; Mortality Rates

In summary, the data indicate that SCID mice injected with $10^6$ BV173 cells and then treated i.v. with bcr-abl antisense phosphorothioate oligodeoxynucleotides 7 or 21 days later (1 mg/mouse for nine consecutive days) were apparently disease-free at 42 and 56 days after the injection of leukemic cells, respectively, whereas the untreated and sense-treated mice has macroscopic, microscopic and molecular evidence of an active leukemic disease process. These differences among the three groups of mice were reflected in their mortality rates.

Figure 12:
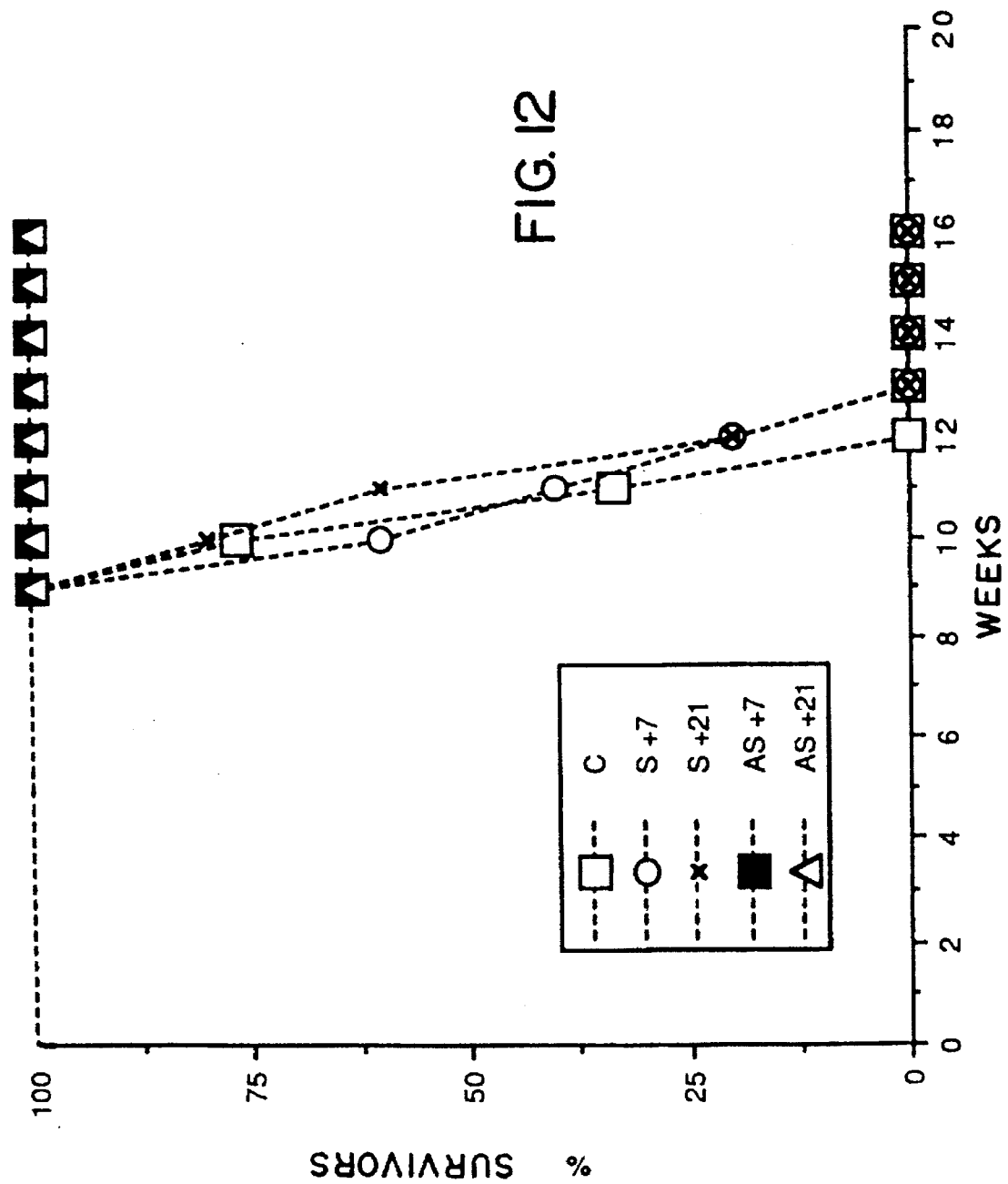
FIG. 12 is a graph of the survival of the same control (-□-), sense-treated (-○-, treatment 7 days post BV173 cell injection; -X-, treatment 21 days post BV173 cell injection; -Δ-, treatment 21 days post BV173 cell injection) and antisense-treated (-■-, treatment 7 days post BV173 cell injection; -▲-, treatment 21 days post BV173 cell injection) mice.

All untreated and bcr-abl sense-treated leukemic mice (3 untreated and 5 sense-treated starting from each of days +7 or +21, for a total of 10 mice), died with diffuse leukemia (confirmed by necroscopy) 10–13 weeks after i.v. injection of $10^6$ BV173 leukemic cells, whereas, bcr-abl antisense-treated mice (6, antisense-treated starting from each of days +7 or +21, for a total of 12 mice) were alive 16 weeks after injection of leukemic cells (FIG. 12) (C, control; S, sense-treated; AS, antisense-treated). Thus, bcr-abl antisense treatment prolonged survival, the hallmark of successful therapy in a fatal disease process.

Figure 8:
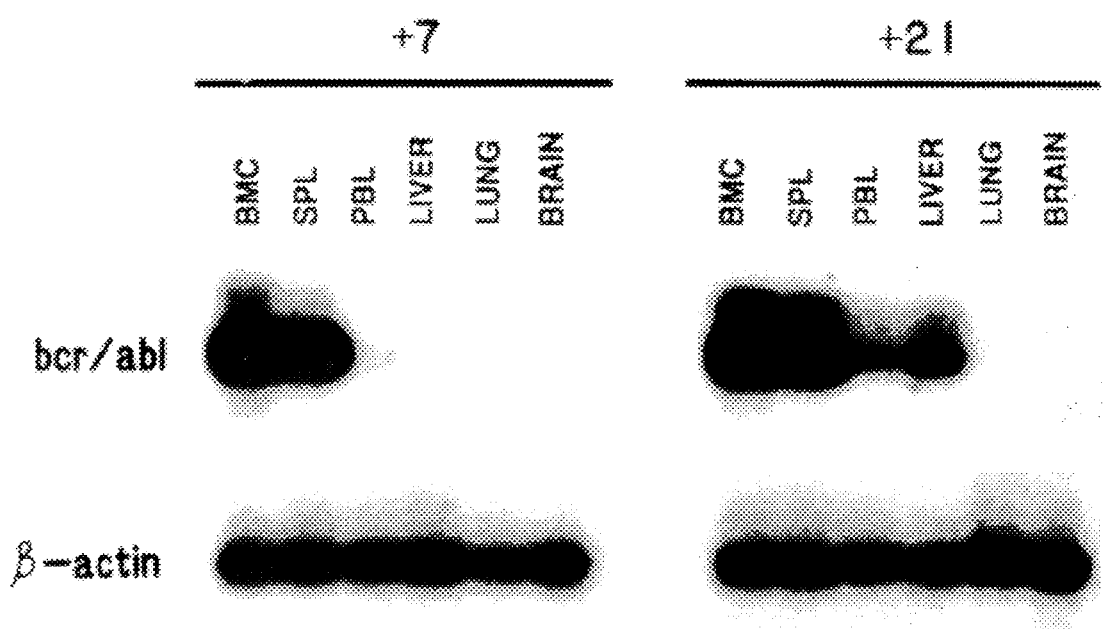
FIG. 8 shows the presence or absence of bcr-abl b2a2 and β-actin mRNA transcripts in various tissues of SCID mice injected at seven (+7) and twenty-one (+21) days after injection with $10^6$ BV173 cells.

At 7 days after injection of $10^6$ BV173 cells, RT-PCR revealed leukemic cells only in cell suspensions derived from bone marrow, spleen and peripheral blood of the mice (FIG. 8, lane +7).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method for treating $Ph^1$-positive leukemia comprising injecting a $Ph^1$-positive leukemia-afflicted individual with an effective amount of about 13-mer to about 26-mer antisense oligonucleotide having a nucleotide sequence complementary to a target sequence of the bcr-abl mRNA transcript of $Ph^1$-positive leukemic cells of the afflicted individual, which target sequence includes the bcr-abl translocation junction and not more that about 13 nucleotides of the abl-derived portion of the transcript, wherein said antisense oligonucleotide hybridizes to said target sequence such that proliferation of $Ph^1$-positive leukemic cells within the afflicted individual is inhibited.

2. A method according to claim 1, wherein the injection comprises intravenous injection.

3. A method according to claim 1 wherein the antisense oligonucleotide comprises an oligodeoxynucleotide.

4. A method according to claim 3 wherein the antisense oligodeoxynucleotide comprises a phosphorothioate oligodeoxynucleotide.

5. A method according to claim 1 wherein the antisense oligonucleotide comprises a phosphoramidite nucleoside.

6. A method according to claim 3 wherein the oligonucleotide is from a 15-mer to a 21-mer.

7. A method according to claim 6 wherein the oligonucleotide is from a 15-mer to an 18-mer.

8. A method according to claim 3 wherein the antisense oligonucleotide contains not more than one nucleotide mismatch with the bcr-abl mRNA target sequence.

9. A method according to claim 8 wherein the antisense oligonucleotide and bcr-abl mRNA target sequence are completely complementary.

10. A method according to claim 3 wherein the bcr-abl mRNA target sequence to which the antisense oligonucleotide hybridizes comprises from about 6 to about 13 abl-derived nucleotides, the balance of said target sequence comprising bcr-derived nucleotides.

11. A method according to claim 10 wherein the bcr-abl mRNA target sequence comprises an about equal number of abl-derived nucleotides and bcr-derived nucleotides.

12. A method according to claim 1 wherein the bcr-abl gene is formed by a translocation between bcr exon 2_ and c-abl exon 2.

13. A method according to claim 12 wherein the antisense oligonucleotide is selected from the group of oligonucleotides having nucleotide sequences consisting of SEQ ID NO:15,
SEQ ID NO:16,
SEQ ID NO:3,
SEQ ID NO:17,
SEQ ID NO:18,
SEQ ID NO:28 and
SEQ ID NO:29.

14. A method according to claim 13 wherein the antisense oligonucleotide has the sequence SEQ ID NO:3.

15. A method according to claim 13 wherein the antisense oligonucleotide comprises a phosphorothioate oligodeoxynucleotide.

16. A method according to claim 1 wherein the bcr-abl gene is formed by a translocation between bcr exon 3 and c-abl exon 2.

17. A method according to claim 16, wherein the antisense oligonucleotide is selected from the group of oligonucleotides having nucleotide sequences consisting of SEQ ID NO:19,
SEQ ID NO:20,
SEQ ID NO:6,
SEQ ID NO:21,
SEQ ID NO:22,
SEQ ID NO:30 and
SEQ ID NO:31.

18. A method according to claim 17 wherein the antisense oligonucleotide has the sequence SEQ ID NO:6.

19. A method according to claim 17 wherein the antisense oligonucleotide comprises a phosphorothioate oligodeoxynucleotide.

20. A method according to claim 1 wherein the bcr-abl gene is formed by a translocation between bcr exon 1 and c-abl exon 2.

21. A method according to claim 20 wherein the antisense oligonucleotide is selected from the group of oligonucleotides having nucleotide sequences consisting of consisting of SEQ ID NO:23,
SEQ ID NO:24,
SEQ ID NO:9,
SEQ ID NO:25,
SEQ ID NO:26,
SEQ ID NO:32, and
SEQ ID NO:33.

22. A method according to claim 21 wherein the antisense oligonucleotide has the sequence SEQ ID NO:9.

23. A method according to claim 21 wherein the antisense oligonucleotide comprises a phosphorothioate oligodeoxynucleotide.

24. A method for treating a $Ph^1$-positive leukemia comprising:

(a) obtaining leukemic cells from a $Ph^1$-positive leukemia-afflicted individual;

(b) extracting RNA sequence encoding a bcr-abl translocation junction from the leukemic cells;

(c) determining the nucleotide sequence of the region of the bcr-abl mRNA transcript surrounding the bcr-abl translocation junction;

(d) preparing an about 13-mer to about 26-mer antisense oligonucleotide having a nucleotide sequence complementary to a target sequence of the bcr-abl mRNA transcript, which target sequence includes the bcr-abl translocation junction and not more than about 13 nucleotides of the abl-derived portion of the transcript; and (e) injecting an effective amount of the antisense oligonucleotide into the afflicted individual such that proliferation of $Ph^1$-positive leukemic cells within the afflicted individual is inhibited.

25. A method for treating a $Ph^1$-positive leukemia comprising intravenously administering to a $Ph^1$-positive leukemia-afflicted individual an effective amount of an about 13-mer to about 26-mer antisense oligonucleotide having a nucleotide sequence complementary to a target sequence of the bcr-abl mRNA transcript of $Ph^1$positive leukemic cells of the afflicted individual, which target sequence includes the bcr-abl translocation junction and not more that about 13 nucleotides of the abl-derived portion of the transcript, wherein said antisense oligonucleotide hybridizes to said target sequence such that proliferation of $Ph^1$-positive leukemic cells within the afflicted individual is inhibited.

26. A method for treating a $Ph^1$-positive leukemia comprising:

(a) obtaining leukemic cells from a $Ph^1$-positive leukemia-afflicted individual;

(b) extracting RNA sequence encoding a bcr-abl translocation junction from the leukemic cells;

(c) determining the nucleotide sequence of the region of the bcr-abl mRNA transcript surrounding the bcr-abl translocation junction;

(d) preparing an about 13-mer to about 26-mer antisense oligonucleotide having a nucleotide sequence complementary to a target sequence of the bcr-abl mRNA transcript, which target sequence includes the bcr-abl translocation junction and not more than about 13 nucleotides of the abl-derived portion of the transcript; and (e) intravenously administering an effective amount of the antisense oligonucleotide to the afflicted individual such that proliferation of $Ph^1$-positive leukemic cells within the afflicted individual is inhibited.

27. A pharmaceutical composition for treating $Ph^1$-positive leukemia comprising a pharmaceutical carrier and an about 13-mer to about 26-mer antisense oligonucleotide having a nucleotide sequence complementary to a target sequence of the mRNA transcript of the human bcr-abl gene, which target sequence includes the bcr-abl translocation junction and not more than about 13 nucleotides of the abl-derived portion of the transcript.

28. A composition according to claim 27 wherein the oligonucleotide comprises an oligodeoxynucleotide.

29. A composition according to claim 28 wherein the antisense oligodeoxynucleotide comprises a phosphorothioate oligodeoxynucleotide.

30. A composition according to claim 27, wherein the oligonucleotide comprises a phosphoramidite nucleoside.

31. A composition according to claim 28 wherein the oligonucleotide is a 15-mer to a 21-mer.

32. A composition according to claim 31 wherein the oligonucleotide is from a 15-mer to an 18-mer.

33. A composition according to claim 28 wherein the oligonucleotide contains not more than one nucleotide mismatch with the bcr-abl mRNA target sequence.

34. A composition according to claim 33 wherein the antisense oligonucleotide and bcr-abl mRNA target sequence are completely complementary.

35. A composition according to claim 28 wherein the bcr-abl mRNA target sequence to which the oligonucleotide hybridizes comprises from about 6 to about 12 c-abl-derived nucleotides, the balance of said target sequence comprising bcr-derived nucleotides.

36. A composition according to claim 35 wherein the bcr-abl mRNA target sequence comprises an about equal number of abl-derived nucleotides and bcr-derived nucleotides.

37. A composition according to claim 28 wherein the antisense oligonucleotide is complementary to the mRNA transcript of a human bcr-abl gene formed by a translocation between bcr exon 2 and c-abl exon 2.

38. A composition according to claim 32 wherein the antisense oligonucleotide is selected from the group of oligonucleotides having nucleotide sequences consisting of

SEQ ID NO:15,

SEQ ID NO:16,

SEQ ID NO:3,

SEQ ID NO:17,

SEQ ID NO:18,

SEQ ID NO:28 and

SEQ ID NO:29.

39. A composition according to claim 38 wherein the antisense oligonucleotide has the sequence SEQ ID NO:3.

40. A composition according to claim 38 wherein the antisense oligonucleotide comprises a phosphorothioate oligodeoxynucleotide.

41. A composition according to claim 28 wherein the antisense oligonucleotide is complementary to the mRNA transcript of a human bcr-abl gene formed by a translocation between bcr exon 3 and c-abl exon 2.

42. A composition according to claim 41 wherein the antisense oligonucleotide is selected from the group of oligonucleotides having nucleotide sequences consisting of

SEQ ID NO:19,

SEQ ID NO:20,

SEQ ID NO:6,

SEQ ID NO:21,

SEQ ID NO:22,

SEQ ID NO:30 and

SEQ ID NO:31.

43. A composition according to claim 42 wherein wherein the antisense oligonucleotide has the sequence SEQ ID NO: 6.

44. A composition according to claim 28 wherein the antisense oligonucleotide is complementary to the mRNA transcript of a human bcr-abl gene formed by a translocation between bcr exon 1 and c-abl exon 2.

45. A composition according to claim 44 wherein the antisense oligonucleotide is selected from the group of oligonucleotides having nucleotide sequences consisting of

SEQ ID NO:23,

SEQ ID NO:24,

SEQ ID NO:9,

SEQ ID NO:25,

SEQ ID NO:26,

SEQ ID NO:32 and

SEQ ID NO:33.

46. A composition according to claim 45 wherein the antisense oligonucleotide has the sequence SEQ ID NO:9.

47. A composition according to claim 45 wherein the antisense oligonucleotide comprises a phosphorothioate oligodeoxynucleotide.

48. A method for treating bone marrow cells from a Ph$^1$-positive leukemia-afflicted individual comprising:

(a) obtaining bone marrow cells from the afflicted individual;

(b) introducing into the bone marrow cells an effective amount of an about 13-mer to about 26-mer antisense oligonucleotide having a nucleotide sequence complementary to a target sequence of the bcr-abl mRNA transcript of Ph$^1$-positive leukemic cells of the afflicted individual, which target sequence includes the bcr-abl translocation junction and not more that about 13 nucleotides of the abl-derived portion of the transcript, wherein said antisense oligonucleotide hybridizes to said target sequence such that proliferation of Ph$^1$-positive leukemic cells is inhibited.

49. A method according to claim 48 wherein the antisense oligonucleotide comprises an oligodeoxynucleotide.

50. A method according to claim 49 wherein the antisense oligodeoxynucleotide comprises a phosphorothioate oligodeoxynucleotide.

51. A method according to claim 49 wherein the oligonucleotide is from a 15-mer to a 21-mer.

52. A method according to claim 51 wherein the oligonucleotide is from a 15-mer to an 18-mer.

53. A method according to claim 49 wherein the antisense oligonucleotide contains not more than one nucleotide mismatch with the bcr-abl mRNA target sequence.

54. A method according to claim 53 wherein the antisense oligonucleotide and bcr-abl mRNA target sequence are completely complementary.

55. A method according to claim 49 wherein the bcr-abl mRNA target sequence to which the antisense oligonucleotide hybridizes comprises from about 6 to about 13 abl-derived nucleotides, the balance of said target sequence comprising bcr-derived nucleotides.

56. A method according to claim 48 wherein the oligonucleotide comprises a phosphoramidite nucleoside.

57. A method according to claim 48 wherein the bcr-abl gene is formed by a translocation between bcr exon 2 and c-abl exon 2.

58. A method according to claim 57 wherein the antisense oligonucleotide is selected from the group of oligonucleotides having nucleotide sequences consisting of

SEQ ID NO:15,

SEQ ID NO:16,

SEQ ID NO:3,

SEQ ID NO:17,

SEQ ID NO:18,

SEQ ID NO:28 and

SEQ ID NO:29.

59. A method according to claim 58 wherein the antisense oligonucleotide has the sequence SEQ ID NO:3.

60. A method according to claim 58 wherein the antisense oligonucleotide comprises a phosphorothioate oligodeoxynucleotide.

61. A method according to claim 48 wherein the bcr-abl gene is formed by a translocation between bcr exon 3 and c-abl exon 2.

62. A method according to claim 61, wherein the antisense oligonucleotide is selected from the group of oligonucleotides having nucleotide sequences consisting of

SEQ ID NO:19,

SEQ ID NO:20,

SEQ ID NO:6,

SEQ ID NO:21,

SEQ ID NO:22,

SEQ ID NO:30 and

SEQ ID NO:31.

63. A method according to claim 62 wherein the antisense oligonucleotide has the sequence SEQ ID NO:6.

64. A method according to claim 62 wherein the antisense oligonucleotide comprises a phosphorothioate oligodeoxynucleotide.

65. A method according to claim 48 wherein the bcr-abl gene is formed by a translocation between bcr exon 1 and c-abl exon 2.

66. A method according to claim 65 wherein the antisense oligonucleotide is selected from the group of oligonucleotides having nucleotide sequences consisting of consisting of

SEQ ID NO:23,

SEQ ID NO:24,

SEQ ID NO:9,

SEQ ID NO:25,

SEQ ID NO:26,

SEQ ID NO:32, and

SEQ ID NO:33.

67. A method according to claim 66 wherein the antisense oligonucleotide has the sequence SEQ ID NO:9.

68. A method according to claim 66 wherein the antisense oligonucleotide comprises a phosphorothioate oligodeoxynucleotide.

69. A method for treating bone marrow cells from a Ph$^1$-positive leukemia-afflicted individual comprising;

(a) obtaining bone marrow cells from the afflicted individual;

(b) extracting RNA sequences encoding a bcr-abl translocation junction from the bone marrow cells;

(c) determining the nucleotide sequence of the region of the bcr-abl mRNA transcript surrounding the bcr-abl translocation junction;

(d) preparing an about 13-mer to about 26-mer antisense oligonucleotide having a nucleotide sequence complementary to a target sequence of the bcr-abl mRNA transcript, which target sequence includes the bcr-abl translocation junction and not more than about 13 nucleotides of the abl-derived portion of the transcript; and (e) introducing into bone marrow cells of the afflicted individual an effective amount of the antisense oligonucleotide such that proliferation of Ph$^1$-positive bone marrow cells is inhibited.

* * * * *